United States Patent [19]

Neuenhofer et al.

[11] Patent Number: 6,013,457
[45] Date of Patent: Jan. 11, 2000

[54] METHOD FOR CARRYING OUT AN IMMUNOASSAY IN A MULTIPHASE SYSTEM

[75] Inventors: Stephan Neuenhofer; Reinhard Käsmarker, both of Marburg, Germany

[73] Assignee: Dade Behring Marburg GmbH, Marburg, Germany

[21] Appl. No.: 08/765,149

[22] PCT Filed: Jun. 23, 1995

[86] PCT No.: PCT/EP95/02447

§ 371 Date: Dec. 23, 1996

§ 102(e) Date: Dec. 23, 1996

[87] PCT Pub. No.: WO96/00393

PCT Pub. Date: Jan. 4, 1996

[30] Foreign Application Priority Data

Jun. 24, 1994 [DE] Germany .............................. 44 21 907

[51] Int. Cl.[7] ..................................................... G01N 33/53
[52] U.S. Cl. .............................. 435/7.1; 435/6; 435/7.71; 435/7.91; 435/7.92; 435/7.93; 435/7.94; 435/7.95; 436/518; 436/523; 436/526; 436/528; 436/531; 436/533; 436/536; 436/537
[58] Field of Search ........................... 435/4, 5, 7.1, 7.71, 435/7.91, 7.92–7.95; 436/514, 518, 523, 526, 528, 531, 533, 536, 537

[56] References Cited

U.S. PATENT DOCUMENTS 4,777,145  10/1988  Luotola et al. .......................... 436/526

FOREIGN PATENT DOCUMENTS

| 0017908 | 10/1980 | European Pat. Off. . |
| 017908 | 10/1980 | European Pat. Off. . |
| 0272691 | 6/1988 | European Pat. Off. . |
| 272691 | 6/1988 | European Pat. Off. . |
| 0328106 | 8/1989 | European Pat. Off. . |
| 328106 | 8/1989 | European Pat. Off. . |
| 0476545 | 3/1992 | European Pat. Off. . |
| 476545 | 3/1992 | European Pat. Off. . |

OTHER PUBLICATIONS

Zhadin et al. "Spectral Manifestations of the Different Types of Binding of Acriflavine with DNA in the Ultraviolet and Visible Region", Conference: Tezisy Doki.–Vses. Konf. Spektrosk. Biopolim., 2nd (1974), pp. 52–53 (Publisher: Akad. Nauk Ukr. SSR, Fiz.–Tekh. Inst. Nizk. Temp., Kharkov, USSR.) Abstract Only.

Granato "PACE (Probe Assay—Chemiluminescence Enhanced)", *Methods Mol. Biol.*, vol. 28(Protocols for Nucleic Acid Analysis by Nonradioactive Probes), (1994), pp. 209–216. Abstract Only.

*Primary Examiner*—Jeffrey Stucker
*Attorney, Agent, or Firm*—Finnegan, Henderson, Farabow, Garrett & Dunner, L.L.P.

[57] ABSTRACT

The present invention relates to a method of carrying out an immunoassay in a multiphase system. Particularly, a sample containing an analyte is brought into contact with a receptor A and a tracer. The analyte can either from a complex with the tracer, or counteract the formation of a complex of receptor A and tracer by competing with the tracer for binding to receptor A, or counteract the formation of a complex of receptor A and tracer by competing with receptor A. Receptor B is added and the signal is determined. In this method, receptor A and receptor B are suitably immobilized, ensuring that the tracer either cannot enter into any binding involving the simultaneous participation of receptors A and B or can enter into such a binding to only such a slight extent that it is nevertheless possible to detect and differentiate differing analyte concentrations.

28 Claims, 24 Drawing Sheets

$[C_{74}H_{88}I_3N_7O_{19}S]^+ [CF_3CO_2]^-$

METHOD FOR CARRYING OUT AN IMMUNOASSAY IN A MULTIPHASE SYSTEM

The present invention relates to a method for carrying out an immunoassay in a multiphase system.

Immunological detection methods have become very important in in vitro diagnostics. The reason for this is that they are highly specific and extremely sensitive. In addition, these assays are easy to implement. The detection methods are based on the immunological interaction between the analyte which is to be detected and its binding partner or partners.

In sandwich assays, the analyte is bound, as in a sandwich, by two different antibodies. One of the two antibodies carries a label (marker) which enables its concentration to be determined.

The sandwich method is not appropriate for small analytes since, for example for steric reasons, two different antibodies are not able to bind to the analyte simultaneously. As a rule, the competitive assays are used under these circumstances. In these assays, an analyte and a synthetic derivative of the analyte, for example, compete for the binding sites of the antibody. As a rule, either the analyte derivative (conventional competitive method) or the antibody (e.g. SPALT: solid phase antigen luminescence technique) is labeled. The labeled component is termed a tracer.

A disadvantage of the known competitive methods is that their sensitivity is relatively low as compared with that of sandwich assays since, in contrast to the situation in immunometric assays, the detection reagents cannot be employed in excess, and it is consequently not possible to displace the equilibrium position to the extent desired in favor of the immune complex to be detected.

As a rule, it is necessary to separate off the excess free tracer antibody (in the case of sandwich assays and when carrying out SPALT) or the unbound analyte tracer (in the case of the conventional competitive method) before measuring the signal emitted by the label.

In the methods known as "homogeneous assays", a separation of this nature is not required since the signals from the free and bound tracers differ from each other.

Heterogeneous assays suffer from the disadvantage that, before measuring the signal which correlates with the analyte concentration, one or more separation steps are required in order to separate off the labeled immune complex, which is usually bound to a solid phase, from the free, labeled reagent. This additional step is relatively laborious when an assay is being carried out manually and increases the susceptibility of the method to error; even when carried out on automated analytical equipment, the step of separation is disadvantageous since an additional subassembly is generally required for this method step.

For this reason, "homogeneous assays" were developed at an early stage. The homogeneous assay, which is known under the designation EMIT (enzyme-multiplied immunoassay technology) (Biochem. Biophys. Res. Commun. 47: 846, 1972), has proved to be of value for detecting small molecules, for example of drugs (e.g. steroids). In a modified EMIT, the activity of the enzyme being used as label decreases when the analyte/enzyme conjugate binds to the antibody which is directed against the analyte. This is apparently due to a diminished affinity of the substrate for the active center of the enzyme in the presence of the antibody, or to steric hindrance, or to a confirmational change in the enzyme.

A further variant of EMIT is based on inhibition of the enzymic activity by the analyte derivative which is bound covalently to the enzyme. In this case, the activity is restored when the antibody which is directed against the analyte binds to the enzyme-labeled analyte derivative. Another variant of this method has been developed for relatively large analytes such as, for example, IgG (Anal. Biochem. 102: 167, 1990). However, the sensitivity which is achieved using this method is fairly low.

FETIA (fluorescence excitation transfer immunoassay; J. Biol. Chem. 251: 4172, 1976) is based on the transfer of energy between two fluorescent molecules, one of which is linked to the antibody while the other is linked to the analyte derivative. In this case, the analyte which is to be detected prevents formation of the complex between the labeled antibody and the labeled analyte derivative.

ECIA (enzyme channelling immunoassay; Anal. Biochem. 25 1056: 223, 1979; Appl. Biochem. Biotechnol. 6, 53–64, 1981) makes use of an antibody and of an analyte tracer each of which carries a different enzyme. The product of the first enzymic reaction constitutes the substrate for the second enzymic reaction. The overall velocity of the two reactions is markedly increased by this co-immobilization.

In SLFIA (substrate-labeled fluorescent immunoassay), an analyte derivative which is labeled with an enzyme substrate competes with the analyte for the binding sites of the anti-analyte antibody. Binding of the substrate-labeled analyte derivative to the antibody prevents the substrate from being reacted enzymically (Burd J. F., Feeney J. E., Carrico R. J., Bogulaski R. C.: Clin. Chem. 23, 1402, 1977; Wong R. C., Burd J. F., Carrico R. J., Buckler R. T., Thoma J., EBogulaski R. C.: Clin. Chem. 25, 686, 1979).

If a fluorescent compound is excited in solution with polarized light, the emission which is observed is also polarized. The degree of this polarization depends on the mobility of the excited molecule. The decreasing mobility of a fluorescent tracer when the latter is bound to an antibody is used, in a fluorescence polarization immunoassay, to differentiate between free and bound tracer.

A fluorescence protection immunoassay (H. E. Ullmann: Tokai J. Exp. Clin. Med., Vol. 4, Supplement, pp. 7–32, 1979) is a homogeneous assay which operates in accordance with the competitive method.

In a conventional competitive assay, sufficient anti-analyte antibodies remain free, when analyte concentrations are low, for binding the tracer in such a manner that the label is no longer accessible to an anti-fluorescein antibody and can consequently no longer be quenched. This steric screening can be made even more effective by coupling the anti-analyte antibodies to a sterically demanding component.

In the solid phase antigen technique, the binding of an unwieldy analyte derivative to the tracer antibody prevents, in an analogous manner, it binding simultaneously to the anti-fluorescein antibody.

In a variant of the fluorescence protection immunoassay, the nonspecific absorption of light by active charcoal due to its coupling to the anti-fluorescein antibody is exploited to increase the quenching effect (scavenging effect).

Other techniques have been described, such as, for example, ALFPIA (antigen-labelled fluorescence protection assay; Clin. Chem. 25: 1077, 1979) or SPA (scintillation proximity assay; U.S. Pat. No. 4,568,649; WO 90/11524), in which a signal is generated by means of a radioactive tracer binding close to a scintillator.

The object underlying this invention was to provide an improved method for carrying out an immunoassay, which method is superior to the known methods, particularly as regards sensitivity, lack of susceptibility to potentially interfering influences and implementation.

The object was achieved by employing, in the present novel method, besides the customary components of an immunoassay which is known from the state of the art, such as, for example, a receptor A which can, for example, be an antigen, an antigen derivative or an antibody, and a tracer which can, independently of the test structure selected, be, for example, a labeled antibody or a labeled antigen, a receptor B as an additional component, which receptor is directed against the label and generates or qualitatively and/or quantitatively alters a signal by interacting with the label. At the same time, suitable immobilization of receptors A and B on one or more phases ensures that the tracer cannot bind simultaneously to receptors A and B. This has the advantage that a tracer which is bound to receptor A and a tracer which is not bound to receptor A can be differentiated directly since they elicit signals which are qualitatively and/or quantitatively different. As a result, it is possible to establish test systems which exhibit a higher sensitivity, a decreased susceptibility to potentially interfering influences and improved implementation as compared to those systems which are known from the state of the art.

The present invention consequently relates to a method for determining an analyte, in which method a sample containing the analyte to be detected is brought into contact with a receptor A and a tracer so that the analyte either a) forms a complex with the tracer, which complex can be detected by the label (immunometric principle), or b) counteracts the formation of a complex of receptor A and tracer by competing with the tracer for binding to receptor A, which is directed against the analyte (competitive principle), or c) counteracts the formation of a complex of receptor A and tracer by competing with receptor A, which is structurally identical to the analyte or structurally similar to the analyte (competitive principle), which comprises additionally 1) adding a receptor B, which generates or qualitatively and/or quantitatively alters a signal by interacting with the label, and 2) determining the signal brought about by the label, with a suitable immobilization of receptors A and B on or in one phase or several phases ensuring that the tracer either cannot enter into any binding involving the simultaneous participation of receptors A and B or can enter into such a binding to only such a slight extent that it is nevertheless possible to detect and differentiate differing analyte concentrations.

In the simplest case, receptor B is an antibody which is directed against the label. However, it is, of course, also possible, when label=enzyme, for receptor B to be an enzyme substrate or an enzyme inhibitor. It is likewise possible, for example, for the label to be a biotinylated enzyme and for receptor B to be an avidin or streptavidin which inhibits the catalytic activity of the enzyme by binding to the biotin residue. That which is always crucial is that the label and receptor B form a "pair" in the sense that their interaction results in the generation of a signal or an alteration to a signal.

Naturally, the positions of label and receptor B can also be switched. For example, the anti-analyte antibody would then, in the case of a SPALT assay, be conjugated to receptor B rather than, as is otherwise customary, labeled with the label, whereas the label is positioned such that only free (i.e. not bound to the solid phase-bound analyte (derivative)) conjugate of anti-analyte antibody and receptor B can bind to the label.

Within the scope of the present inventor, a tracer is, in its most general form, understood to be a labeled receptor. In this context the label can be bound covalently or non-covalently to the receptor. All the tracers, and also receptors and labels, which are known from the state of the art can be employed in accordance with the invention provided that they are only combined with each other in a manner which is meaningful and with which the skilled person is familiar. The receptor moiety of the tracer can either be a single receptor or consist of two or more receptors which can in turn be linked to each other either covalently or non-covalently.

A label is understood to mean a compound which is capable of emitting a signal or of directly or indirectly generating a signal; for example a luminogenic group or an enzyme.

In the case of a conventional competitive assay, the equilibrium of the analyte-specific immune reaction can, in the method described herein, be shifted in favor of the immune complexes to be detected using an additional, linked-in immune reaction. In the simplest case, this is achieved by the analyte displacing an analyte tracer from the binding site of an antibody A, and the analyte tracer, which has thus been "extracted" being bound by an antibody B in an additional immune reaction.

Whereas antibody A is directed against analyte and analyte tracer, antibody B is only able to bind the analyte tracer. As a result, the analyte tracer is no longer able to participate in the customary manner in the equilibrium reaction "antibody A/analyte/analyte tracer".

By virtue of this specificity, which is only directed against the analyte tracer, of antibody B, and by means of choosing a suitably high concentration of the antibody B, the position of the equilibrium can be influenced in a very favorable manner. This thereby reduces the disadvantages of a normal competitive immune reaction as regards sensitivity. If the signal emitted by the label is altered as a result of the tracer being bound to antibody B, there is then no need to separate off the component to be measured, since, in this case, the change in signal correlates with the concentration of the analyte to be determined. The alteration of the emitted signal can either be elicited directly by the binding to antibody B or be elicited by the tracer being brought into a signal-modulating environment by means of the binding to antibody B. In the case of a fluorescence quenching effect, this can be achieved, for example, by conjugating antibody B with a quenching substance.

In the case of a sandwich assay, the number of sandwich complexes (composed of capturing antibody A, analyte and tracer antibody) which are formed correlates with the concentration of the analyte. Consequently, the remaining quantity of tracer which is not bound in the sandwich complex also correlates with the analyte concentration. This free tracer is bound by antibody B.

In the present invention, an appropriate immobilization of the two receptors A and B ensures that tracers are not able to enter into any stable immune complexes in which receptors A and B are participating simultaneously (for example sandwich complex composed of antibody A, analyte tracer and antibody B). One possibility for achieving this is to couple receptors A and B to different particles with the size and composition of the particles being chosen such that a binding of the tracer in which receptors A and B participate simultaneously is rendered more difficult or prevented.

Furthermore, receptors A and B can also be bound to the same solid phase, but at a distance which is large enough to render more difficult or prevent such a binding to a tracer in which receptors A and B participate simultaneously.

Figure 1:
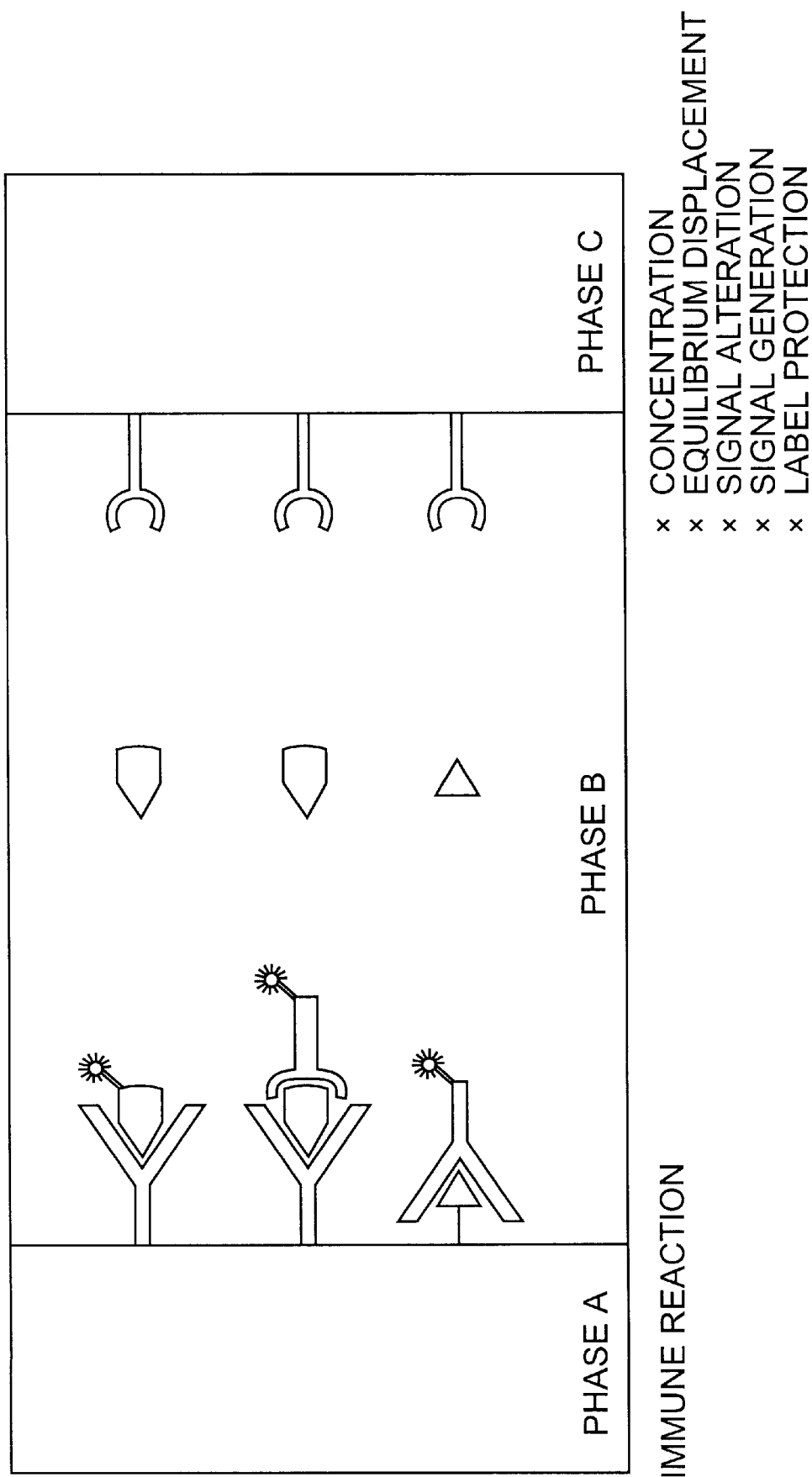
FIG. 1 shows the basic principle of a multiphase assay system.

By way of example, the principles of some possible options are depicted diagrammatically in FIG. 1.

Examples of such spatial arrangements are:

1. Attachment of antibody A and antibody B to different plastic beads, with the size or the mass of the beads being chosen to be so large such that it is impossible for two beads to be stably bridged by a bond in which antibody A and antibody B mutually participate or that, for steric reasons, it is impossible for sufficient antibody B-coated beads to bind to an antibody A-coated bead.

2. Attachment of antibody A to a plastic bead and attachment of antibody B to the internal wall of the reaction tube.

The following is an example of an option for implementing a heterogeneous assay:

Plastic beads, which are coated with immobilized antibody A (anti-analyte antibody) which has previously been saturated with analyte tracer, are added to a polystyrene tube which is coated with antibody B (=anti-label antibody). After adding the sample, containing the analyte, and incubation buffer, the suspension is incubated and the plastic beads are then removed. The signal remaining in the tube is measured.

Figure 2B:
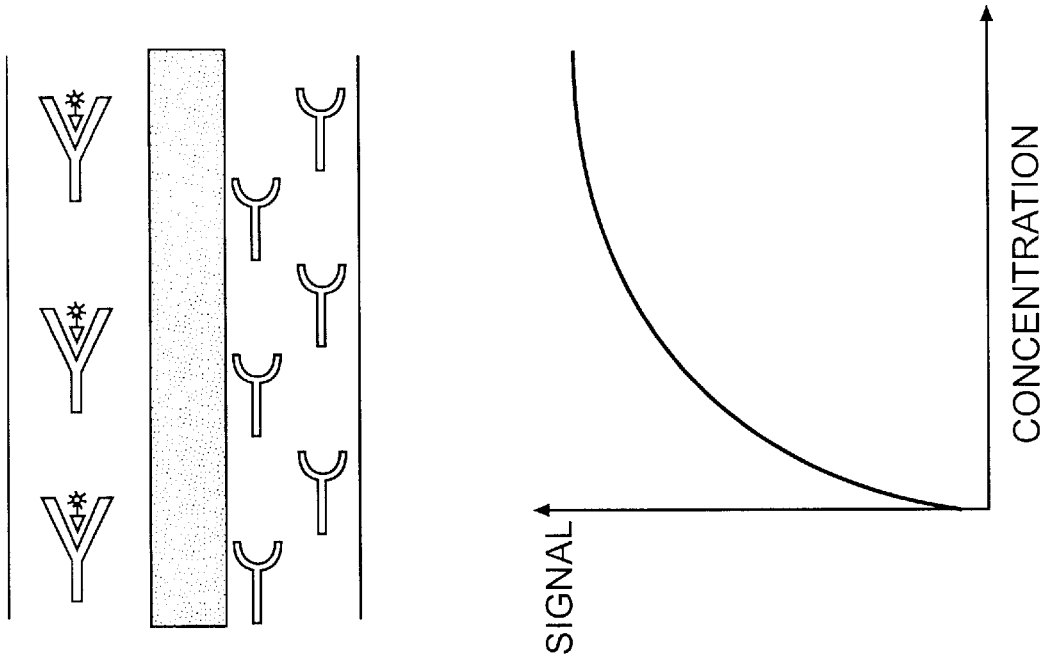
FIG. 2 shows the OPUS assay.
Figure 2A:
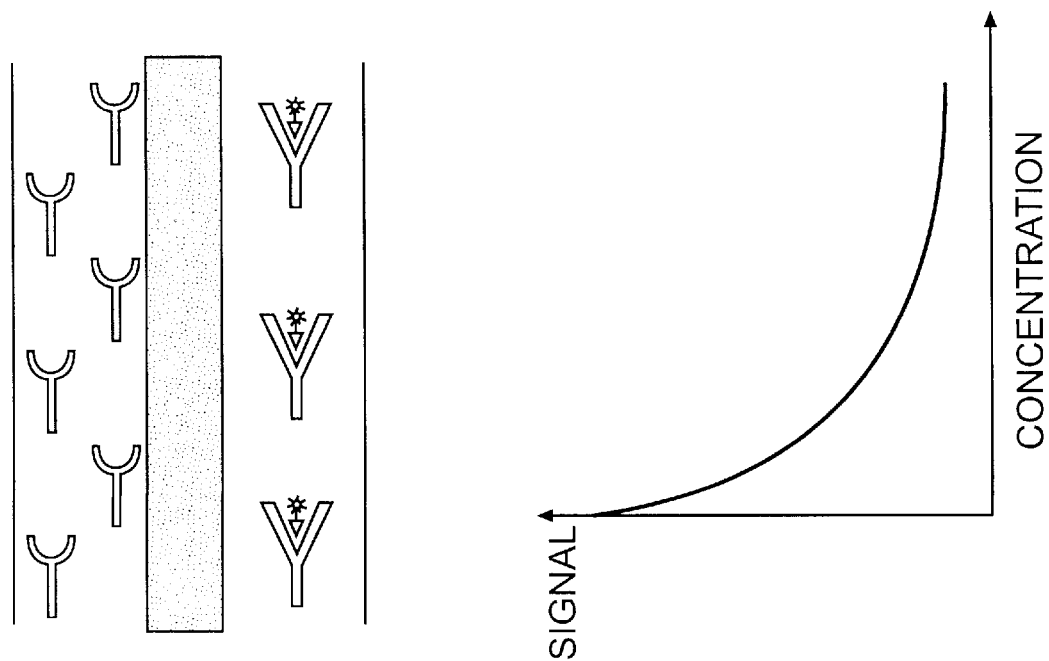

3. Fixing of antibody A and antibody B in different gel phases of a test element, as is employed, for example, in the OPUS® system (from BDI, Westwood, Mass., USA.) (FIG. 2).

3a. An OPUS test module is modified in the following manner: Anti-fluorescence label antibodies (B antibodies) are embedded in the top layer of agarose, the middle layer serves, as usual, as the optical filter, and immune complexes composed of anti-analyte antibody (antibody A) and fluorescence-labeled analyte tracer are embedded in the bottom layer.

Analytes from the sample which is loaded on displace the tracer molecules from the immune complexes; the tracers diffuse out of the bottom layer and are bound by the anti-fluorescence label antibodies in the top layer. The fluorescence signal of the bottom layer is measured. This results in a standard curve which declines as the analyte concentration increases.

3b. An OPUS test module is modified in the following manner: anti-fluorescence label antibodies (B antibodies) are embedded in the bottommost agarose layer, the middle layer serves, as usual, as the optical filter, and immune complexes composed of anti-analyte antibody (antibody A) and fluorescence-labeled analyte tracer are embedded in the top layer.

Analytes from the sample which is loaded on displace the tracer molecules from the immune complexes; the tracers diffuse into the bottom layer and are bound by the anti-fluorescence label antibodies. The fluorescence signal of the bottom layer is measured. This results in a standard curve which rises with increasing analyte concentration.

4. Attachment of antibody A and antibody B to membrane fibers, with the distance between antibody A and antibody B on a fiber ensuring that the two antibodies cannot simultaneously enter into a bond with a tracer.

Figure 3:
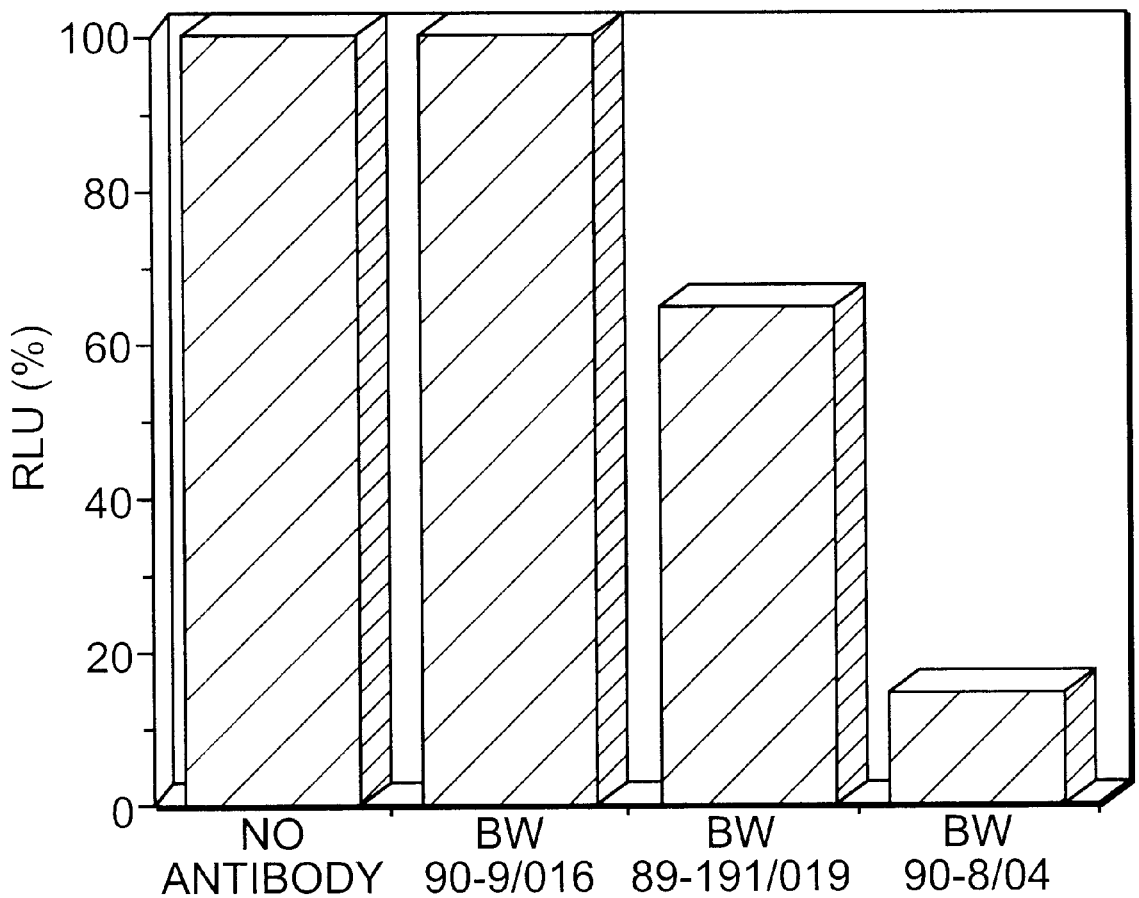
FIG. 3 shows the signal quench produced by anti-label antibodies.

If the binding of the tracer to the antibody B brings about a change in the signal which is emitted by the tracer, the assay can then be carried out in such a manner that a separation and/or washing step becomes superfluous. In this case, the change in the signal correlates with the concentration of the analyte to be determined. The change in the signal can be a qualitative signal change, for example a shift in the emission wavelength, and/or a quantitative signal change, for example a signal quench. The latter is depicted in FIG. 3 using the example of an acridinium acylsulfonamide label.

If the label/anti-label antibody pair is replaced by an enzyme/enzyme substrate pair, a signal can then be generated instead of there being a change in signal.

Figure 4:
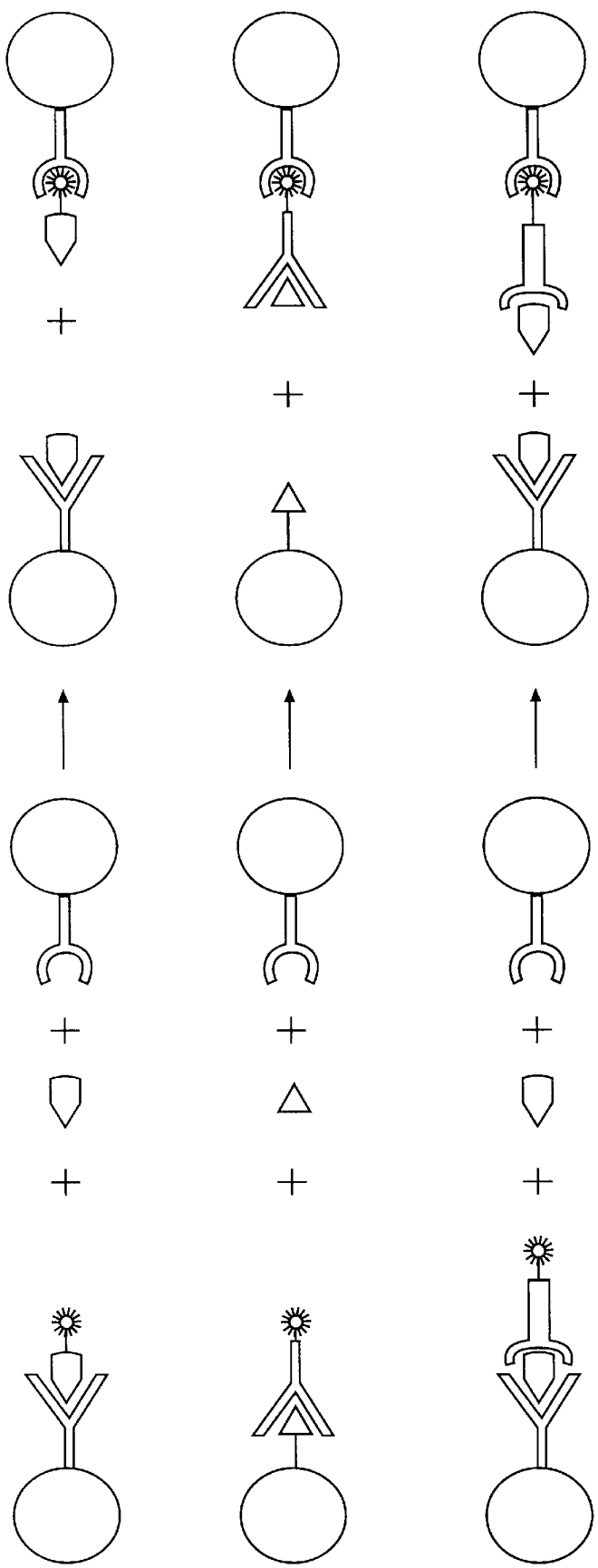
FIG. 4 shows homogeneous assays in a multiphase system.

The incubation (steps) can be carried out in a variety of ways; the choice of sequence is, as in the case of the heterogeneous implementation, part of the normal optimization work. Examples are:

1. A preformed complex composed of antibody A (bound to a solid phase) and analyte tracer is incubated with the sample which contains analyte. Antibody B (likewise bound to a solid phase) is either present from the beginning of this incubation or else only added after the passage of a certain time $t_1$. The signal is measured after a time $t_2$ (see top line in FIG. 4)

2. A preformed complex composed of analyte derivative (bound to a solid phase) and labeled antibody A (SPALT principle) is incubated with the sample-containing analyte. Antibody B (likewise bound to a solid phase) is either present from the beginning of this incubation or else is only added after the passage of a certain time $t_1$. The signal is measured after a time $t_2$ (see middle line in FIG. 4).

3. A preformed complex composed of antibody A (bound to a solid phase), analyte and tracer antibody, that is a preformed sandwich complex, is incubated with the sample containing analyte and with antibody B (likewise bound to a solid phase). A modified analyte can also be employed in place of the analyte in the preformed sandwich complex in order to destabilize the preformed complex and thereby facilitate displacement of the tracer (see bottom line in FIG. 4).

Figure 5:
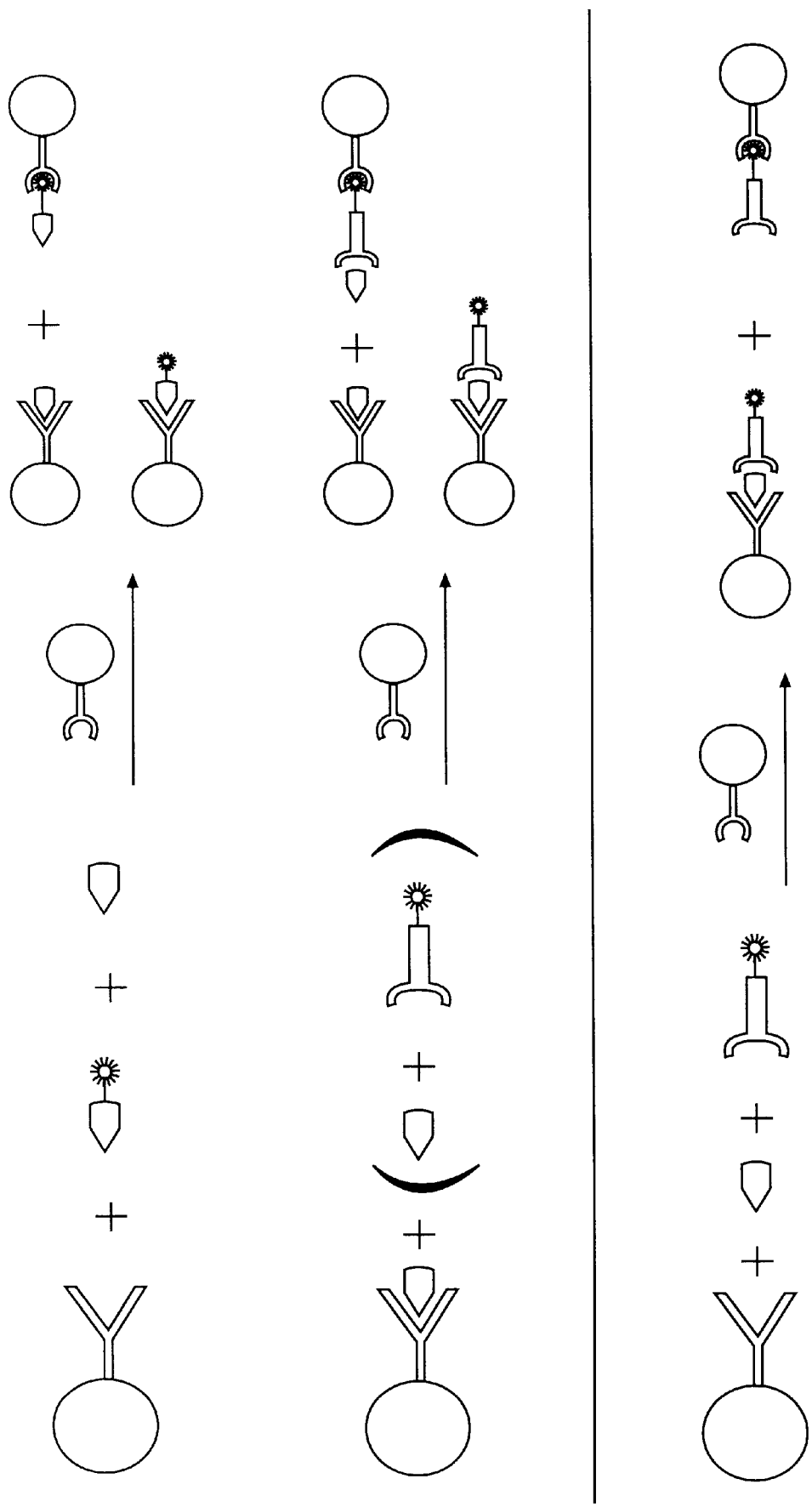
FIG. 5 shows additional examples of homogeneous assays in a multiphase system.

4. Antibody A (bound to a solid phase), analyte tracer and sample containing analyte are incubated together. After the passage of a certain time $t_1$, antibody B (likewise bound to a solid phase) is added, and the signal is measured after the passage of a time $t_2$ (see top line in FIG. 5).

5. The sample containing analyte, and the tracer antibody, are incubated together and, after the passage of a certain time $t_1$, a preformed complex composed of antibody A (bound to a solid phase) and analyte is added. After the passage of a time $t_2$, antibody B (likewise bound to a solid phase) is added, and the signal is measured after a time $t_3$ (see middle line in FIG. 5).

6. Antibody A (bound to a solid phase), the sample containing the analyte, and the tracer antibody, are incubated. Once the sandwich complexes have formed, antibody B (likewise bound to a solid phase) is added, as a result of which that portion of the tracer which is not bound in the sandwich complex becomes bound by antibody B (see bottom line in FIG. 5).

7. A preformed complex composed of antibody A (bound to a solid phase) and analyte or analyte derivative is incubated together with the sample containing the analyte and with an analyte tracer. That portion of the tracer which is not bound by antibody A becomes bound by antibody B.

On top of this, the implementation of the assay can be varied by linking an additional immune reaction between the tracer and an additional antibody B' into the immune reaction between the tracer and antibody B. While the solid-phase-bound antibody B, for example, has the function of binding that free portion of the tracer which remains following or during the analyte-specific immune reaction, in order to protect the signal of this tracer portion from any change, the signal of the tracer involved in the analyte-specific bond can be selectively altered by adding an antibody B' which is not bound to a solid phase.

This additional incubation step can be of advantage for, in a manually executed assay for example, being able to control more precisely the time during which antibody B exerts its effect, and/or, by means of appropriately high concentrations of antibody B', bringing about a more rapid and/or more clearly pronounced change in signal, for example in cases in which the quantity of antibody B which is present or can be added is limited due to the fact that the antibody is bound to a solid phase.

Some relevant examples are listed below:

8. A preformed complex composed of antibody A (bound to a solid phase) and analyte tracer is incubated with the sample containing analyte. Antibody B (bound to a different solid phase) is either present from the beginning of this incubation or else is only added after the passage of a certain time $t_1$. After a time $t_2$, an antibody B' is added and the signal is measured after a suitable time $t_3$.

Figure 6:
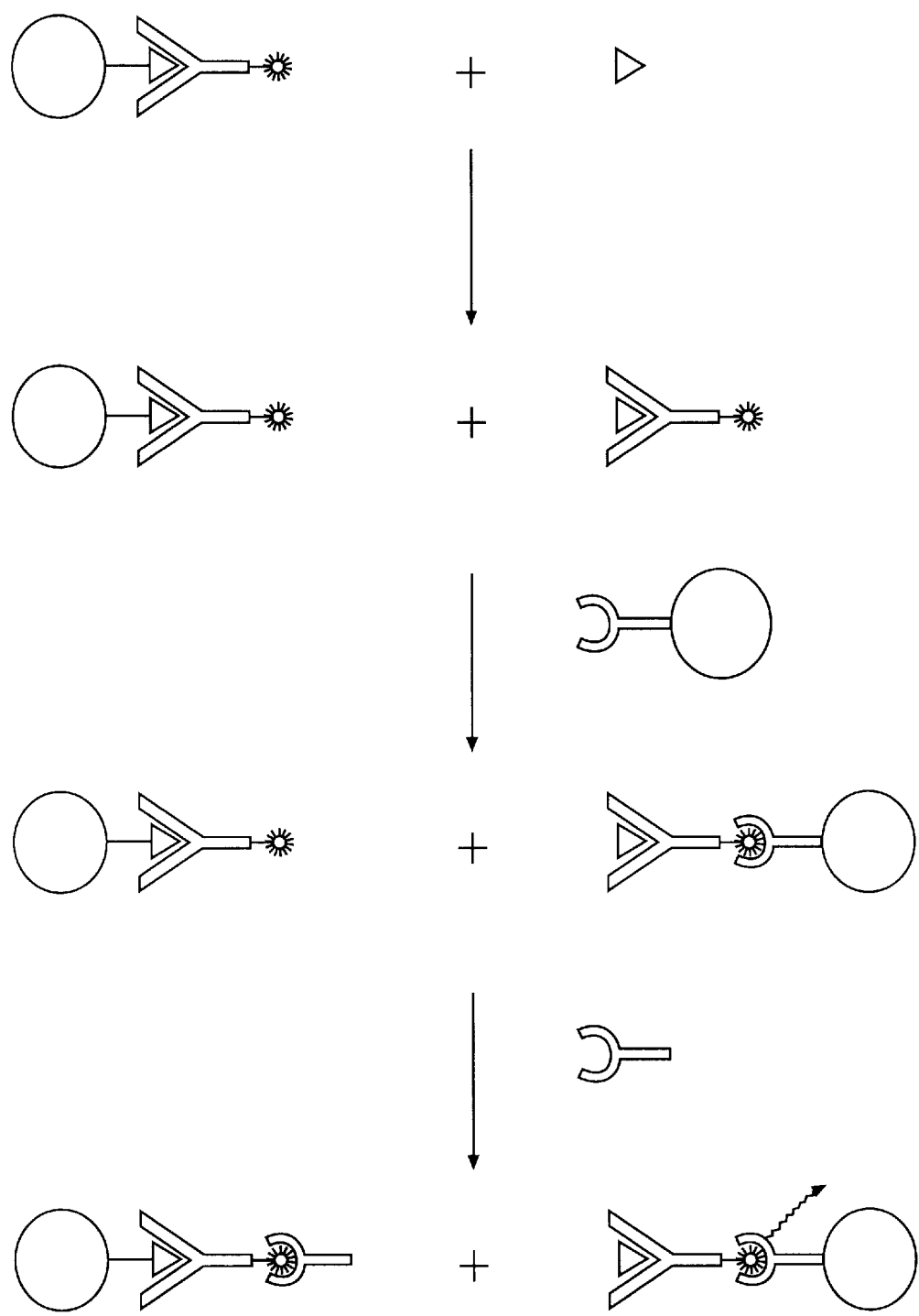
FIG. 6 shows another example of a homogeneous assay in a multiphase system.

9. A preformed complex composed of analyte derivative (bound to a solid phase) and labeled antibody A (SPALT principle) is incubated with the sample containing analyte. Antibody B (likewise bound to a solid phase) is either present from the beginning of this incubation or is only added after the passage of a certain time $t_1$. After a time $t_2$, an antibody B' is added and the signal is measured after a further incubation time $t_3$ (see FIG. 6).

10. A preformed complex composed of antibody A (bound to a solid phase), analyte and tracer antibody, that is a preformed sandwich complex, is incubated with the sample containing analyte and with antibody B (likewise bound to a solid phase). Antibody B' is then added and the signal is measured.

11. Antibody A (bound to a solid phase), analyte tracer and sample containing analyte are incubated together. After the passage of a certain time $t_1$, antibody B (likewise bound to a solid phase) is added, and antibody B' is added after the passage of a time $t_2$. The signal is then measured.

12. The sample containing analyte, and tracer antibody, are incubated together and, after the passage of a certain time $t_1$, a preformed complex composed of antibody A (bound to a solid phase) and analyte is added. After the passage of a time $t_2$, antibody B (likewise bound to a solid phase) is added, and antibody B' is added after a time $t_3$. The signal is then measured.

13. Antibody A (bound to a solid phase), the sample containing the analyte, and tracer antibody, are incubated. Once the sandwich complexes have been formed, antibody B (likewise bound to a solid phase) is added, as a result of which that portion of the tracer which is not bound in the sandwich complex becomes bound by antibody B. When antibody B' is added, this antibody binds to the tracer which is involved in the sandwich complex.

If the label group of the tracer is an enzyme, antibody B can then be replaced by an enzyme substrate. In this case, a signal is generated as a result of contact between tracer and enzyme substrate. In this case too, the signal which is generated correlates with the concentration of the analyte to be determined. Examples of this are:

14. A preformed complex composed of antibody A (bound to a solid phase) and analyte tracer (analyte derivative labeled with an enzyme) is incubated with the sample containing analyte. An enzyme substrate, which is immobilized on a different solid phase, is either present from the beginning of this incubation or else only added after the passage of a certain time $t_1$. After a time $t_2$, the signal is measured.

15. A preformed complex composed of analyte derivative (bound to a solid phase) and enzyme-labeled antibody A (SPALT principle) is incubated with the sample containing analyte. An enzyme substrate, which is bound to a different solid phase, is either present from the beginning of this incubation or else is only added after the passage of a certain time $t_1$. After a time $t_2$, the signal is measured.

16. A preformed complex composed of antibody A (bound to a solid phase), analyte and tracer antibody, that is a preformed sandwich complex, is incubated with the sample containing analyte and with an enzyme substrate (likewise bound to a solid phase).

17. Antibody A (bound to a solid phase), analyte tracer and sample containing analyte are incubated together. After the passage of a certain time $t_1$, an enzyme substrate (likewise bound to a solid phase) is added, and the signal is measured after the passage of a time $t_2$.

18. The sample containing the analyte, and tracer antibody, are incubated together and, after the passage of a certain time $t_1$, a preformed complex composed of antibody A (bound to a solid phase) and analyte is added. After the passage of a time $t_2$, an enzyme substrate (likewise bound to a solid phase) is added, and the signal is measured after a time $t_3$.

19. Antibody A (bound to a solid phase), the sample containing the analyte, and tracer antibody, are incubated. Once the sandwich complexes have been formed, an enzyme substrate B (likewise bound to a solid phase) is added, and, as a result, that portion of the tracer which is not bound in the sandwich complex is able to react with the enzyme substrate.

20. A preformed complex composed of antibody A (bound to a solid phase) and analyte tracer is incubated with the sample containing analyte. An antibody B (likewise bound to a solid phase), which is directed against the enzyme and diminishes or inhibits the enzymic activity, is either present from the beginning of this incubation or else only added after the passage of a certain time $t_1$. After a time $t_2$, an enzyme substrate is added and the signal is measured after a suitable time $t_3$.

21. A preformed complex composed of analyte derivative (bound to a solid phase) and enzyme-labeled antibody A (SPALT principle) is incubated with the sample containing analyte. The antibody B (likewise bound to a solid phase), which is directed against the enzyme, is either present from the beginning of this incubation or else only added after the passage of a certain time $t_1$. After a time $t_2$, an enzyme substrate is added and the signal is measured after a further incubation time $t_3$.

22. A preformed complex composed of antibody A (bound to a solid phase), analyte and tracer antibody, that is a preformed sandwich complex, is incubated with the sample containing analyte and with antibody B (directed against the enzyme and likewise bound to a solid phase). An enzyme substrate is then added and the signal is measured.

23. Antibody A (bound to a solid phase), analyte tracer and sample containing analyte are incubated together. After the passage of a certain time $t_1$, antibody B (directed against the enzyme and likewise bound to a solid phase) is added, and an enzyme substrate is added after the passage of a time $t_2$. The signal is then measured.

24. The sample containing analyte, and tracer antibody, are incubated together, and, after the passage of a certain time $t_1$, a preformed complex composed of antibody A (bound to a solid phase) and analyte is added. After the passage of a time $t_2$, antibody B (directed against the enzyme and likewise bound to a solid phase) is added, and an enzyme substrate is added after a time $t_3$. The signal is then measured.

25. Antibody A (bound to a solid phase), the sample containing the analyte, and tracer antibody, are incubated. Once the sandwich complexes have been formed, antibody B (directed against the enzyme and likewise bound to a solid phase) is added, and, as a result, that portion of the tracer which is not bound in the sandwich complex becomes bound by antibody B. By means of adding an enzyme substrate, the tracer involved in the sandwich complex can generate a signal.

All the examples cited here can, of course, be implemented in a variant in which the positions of the label and of receptor B are interchanged. The following are examples of this:

26. A preformed complex composed of antibody A (bound to a solid phase) and an analyte derivative conjugated with receptor B is incubated with the sample containing analyte. The label (likewise bound to a solid phase) is either present from the beginning of this incubation or else only added after the passage of a certain time $t_1$. After a time $t_2$, the signal is measured.

27. A preformed complex composed of analyte derivative (bound to a solid phase) and an antibody A conjugated with antibody B (SPALT principle) is incubated with the sample containing analyte. The label (likewise bound to a solid phase) is either present from the beginning of this incubation or else only added after the passage of a certain time $t_1$. After a time $t_2$, the signal is measured.

28. A preformed complex composed of antibody A (bound to a solid phase), analyte and anti-analyte antibody labeled with antibody B, that is a preformed sandwich complex, is incubated with the sample containing analyte and with the label (likewise bound to a solid phase).

29. Antibody A (bound to a solid phase), an analyte derivative conjugated with antibody B, and sample containing analyte, are incubated together. After the passage of a certain time $t_1$, the label (likewise bound to a solid phase) is added, and the signal is measured after the passage of a time $t_2$.

30. The sample containing analyte, and an anti-analyte antibody conjugated with antibody B are incubated together and, after the passage of a certain time $t_1$, a preformed complex composed of antibody A (bound to a solid phase) and analyte is added. After the passage of a time $t_2$, the label (likewise bound to a solid phase) is added, and the signal is measured after a time $t_3$.

31. Antibody A (bound to a solid phase), the sample containing the analyte, and an anti-analyte antibody conjugated with antibody B are incubated. Once the sandwich complexes have been formed, the label (likewise bound to a solid phase) is added, and, as a result, that portion of anti-analyte antibody conjugated with antibody B which is not bound in the sandwich complex is enabled to bind the label.

32. A preformed complex composed of antibody A (bound to a solid phase) and analyte derivative labeled with enzyme substrate is incubated with the sample containing analyte. An enzyme, which is immobilized on a different solid phase, is either present from the beginning of this incubation or else only added after the passage of a certain time $t_1$. After a time $t_2$, the signal is measured.

33. A preformed complex composed of analyte derivative (bound to a solid phase) and enzyme-substrate-labeled antibody A (SPALT principle) is incubated with the sample containing analyte. An enzyme, which is bound to a different solid phase, is either present: from the beginning of this incubation or else only aided after the passage of a certain time $t_1$. After a time $t_2$, the signal is measured.

34. A preformed complex composed of antibody A (bound to a solid phase), analyte and enzyme-substrate-labeled anti-analyte antibody, that is a preformed sandwich complex, is incubated with the sample containing analyte and with an enzyme (likewise bound to a solid phase).

35. Antibody A (bound to a solid phase, an analyte derivative labeled with enzyme substrate, and sample containing analyte are incubated together. After the passage of a certain time $t_1$, an enzyme likewise bound to a solid phase) is added, and the signal is measured after the passage of a time $t_2$.

36. The sample containing analyte, and anti-analyte antibody which is labeled with enzyme substrate are incubated together, and, after the passage of a certain time $t_1$, a preformed complex composed of antibody A (bound to a solid phase) and analyte is added. After the passage of a time $t_2$, an enzyme (likewise bound to a solid phase) is added, and th e signal is measured after a time $t_3$.

37. Antibody A (bound to a solid phase), the sample containing the analyte, and enzyme-substrate-labeled anti-analyte antibody are incubated. Once the sandwich complexes have been formed, an enzyme (likewise bound to a solid phase), is added, and, as a result, that portion of enzyme-substrate-labeled antibody which is not bound in the sandwich complex is enabled to react with the enzyme.

38. A preformed complex composed of antibody A (bound to a solid phase) and enzyme-substrate-labeled analyte derivative is incubated with the sample containing analyte. An antibody B which is directed against the enzyme substrate (inhibits or prevents enzymic conversion of the enzyme substrate by binding to it; antibody B likewise bound to a solid phase) is either present from the beginning of this incubation or else only added after the passage of a certain time $t_1$. An enzyme is added after a time $t_2$, and the signal is measured after a suitable time $t_3$.

Figure 7:
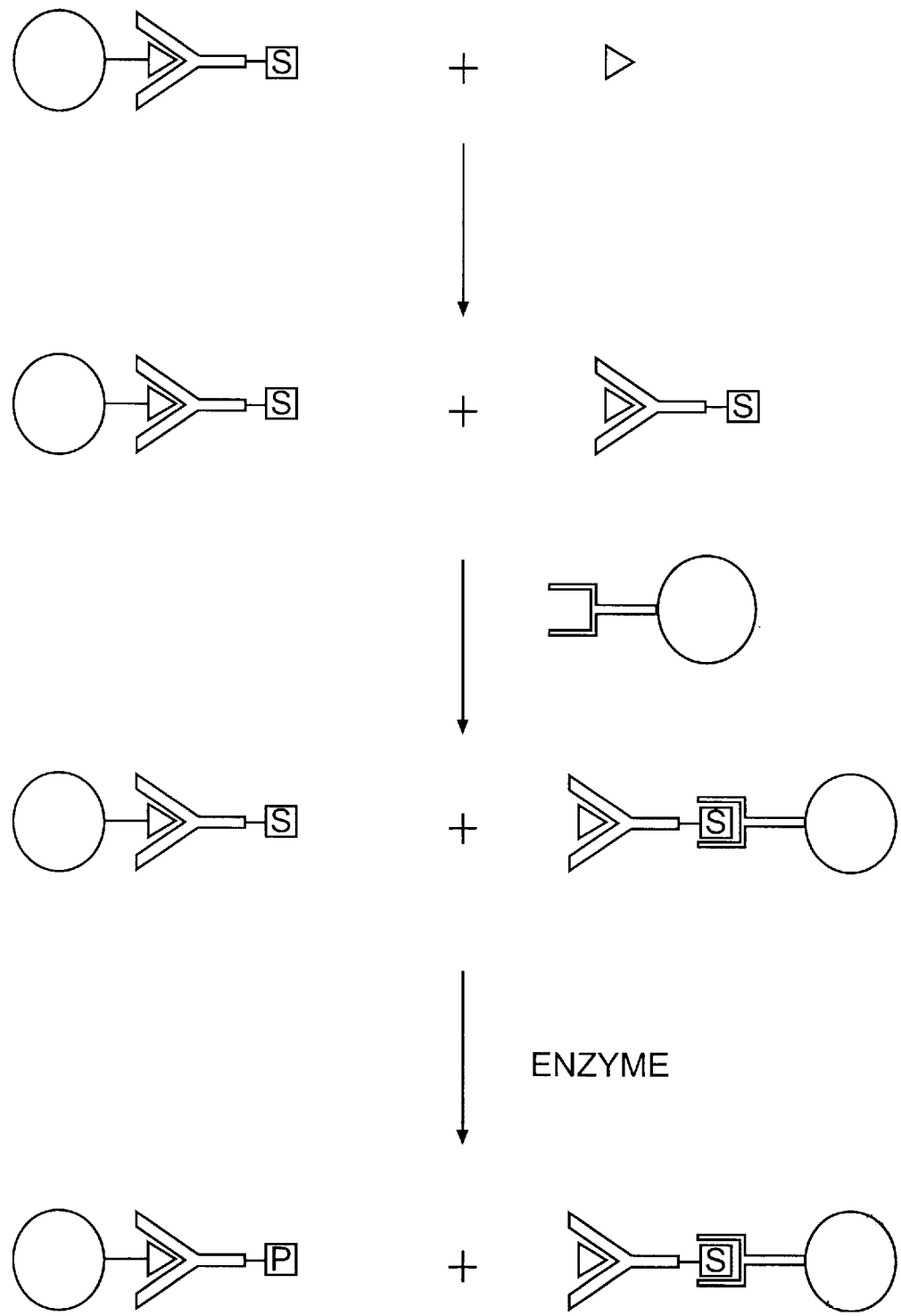
FIG. 7 shows a variations of the assay of FIG. 6.

39. A preformed complex composed of analyte derivative (bound to a solid phase) and enzyme-substrate-labeled antibody A (SPALT principle) is incubated with the sample containing analyte. The antibody B (bound to a different solid phase) which is directed against the enzyme substrate is either present from the beginning of this incubation or else only added after the passage of a certain time $t_1$. An enzyme is added after a time $t_2$, and the signal is measured after a further incubation time $t_3$ (see FIG. 7).

40. A preformed complex composed of antibody A (bound to a solid phase), analyte, and anti-analyte antibody which is labeled with enzyme substrate, that is a preformed sandwich complex, is incubated with the sample containing analyte and with antibody B (directed against the enzyme substrate and likewise(bound to a solid phase). An enzyme is then added and the signal is measured.

41. Antibody A (bound to a solid phase), an analyte derivative which is labeled with enzyme substrate, and sample containing analyte are incubated together. After the passage of a certain time $t_1$, antibody B (directed against the enzyme substrate and likewise bound to a solid phase) is added, and an enzyme is added after the passage of a time $t_2$. The signal is then measured.

42. The sample containing analyte, and anti-analyte antibody which is labeled with enzyme substrate are incubated together and, after the passage of a certain time $t_1$, a preformed complex composed of antibody A (bound to a solid phase) and analyte is added. After the passage of a time $t_2$, antibody B (directed against the enzyme substrate and likewise bound to a solid phase) is added, and an enzyme is added after a time $t_3$. The signal is then measured.

43. Antibody A (bound to a solid phase), the sample containing the analyte, and enzyme-substrate-labeled anti-analyte antibody are incubated. Once the sandwich complexes have been formed, antibody B (directed against the enzyme substrate and likewise bound to a solid phase) is added, and, as a result, that portion of enzyme-substrate-labeled antibody which is not bound in the sandwich complex becomes bound by antibody B. When an enzyme is added, the tracer involved in the sandwich complex can generate a signal.

The present invention is additionally described by the examples below, which are intended to further elucidate the invention while in no way restricting it, and by the patent claims.

EXAMPLE 1

Luminescence Immunoassay (LIA) for Determining PSA

Preparation of the Reagents:

Solid phase A:

Magnetic particles from Rhône-Poulenc, (Catalog No. EM1-100/40) were coated with a monoclonal anti-PSA antibody (BW 92-283/029; Behringwerke AG, Marburg) using the carbodiimide method (G. Wendlberger et al., Synthese von Peptiden [Synthesis of pepzides], Part 2, Methoden Org. Chem. [Methods of organic chemistry] (Houben-Weyl) 4th ed. 1952, Vol. XV/2, 1974). The coating concentration was 6 mg of antibody per ml of 10% magnetic particle suspension. The ready-to-use suspension had a magnetic particle concentration of 2.5 mg per ml of storage buffer. (50 mm 2-cyclohexylaminoethanesulfonic acid (CHES), 0.5 g of NaN$_3$/l, 3 g of bovine serum albumin/l, pE 8.0).

Solid phase B:

Magnetic particles were coated, as in the case of solid phase A, with a monoclonal antibody which is directed against the acridinium N-acylsulfonamide label (EP-A-0 257 541 and EP-A-0 330 050) (BW 90-9/04; Behringwerke AG; deposited in the Deutsche Sammlung von Mikroorganismen und Zellkulturen GmbH [German Collection of Microorganisms and Cell Cultures], Braunschweig, Germany, under deposition number DSM ACC 2184).

Tracer;

A monoclonal anti-PSA antibody (BW 92-284/03, Behringwerke AG) was labeled with the acridinium N-acylsulfonamide label (EP-A-0 257 541 and EP-A-0 330 050) in a molar ratio of 1+1. The labeling was carried out in accordance with the NHS method, which is described in the literature (NHS=N-hydroxysuccinimide reactive group; A. K. Campbell, Chemiluminescence: Principles and Applications in Biology and Medicine, 1st edition, VCH/Horwood, Weinheim/Chichester, 1988, p. 439). Gel permeation chromatography (Sephadex G 25) was used for the purification. The tracer was stored at a concentration of 300 ng/ml of tracer buffer (10 mM sodium acetate, 150 mM NaCl, 2 g of bovine serum albumin/l, 0.1% Mergal K9N, pH 5.0).

PSA standards:

The buffer in which PSA (prostate-specific antigen, Behringwerke AG) was dissolved had the following composition: 50 mM Tris, 150 mM NaCl, 0.05% NaN$_3$, 0.01% Tween 20, 0.5 g of bovine IgG/l, 40 g of bovine serum albumin/l, 8 mg of Titriplex V/l, pH 7.6. The standard concentrations were 0, 50, 100, 200 and 400 ng/ml.

Preformed complex:

The preformed complex composed of anti-PSA antibody (bound to solid phase A) and PSA was formed as follows: 1 ml of the solid phase A suspension and 1 ml of PSA solution [20 mg/ml (10 mM phosphate buffer, pH 7.3, containing 1 g of bovine IgG/l and 0.5 g of sodium azide/l)] were incubated at 37° C. for 30 minutes, and the particles were then washed 5' with 1 ml of buffer (magnetic separation), and made up to a final volume of 1 ml.

Assay implementation:

10 ml of sample containing PSA were incubated at RT for 2 minutes with 10 ml of tracer. 10 ml of the preformed complex were then added, followed by 10 ml of solid phase B after a further 2 minutes. The sample was subsequently measured in a luminometer (BeriLux® analyzer) (measuring time 1 s).

Figure 8:
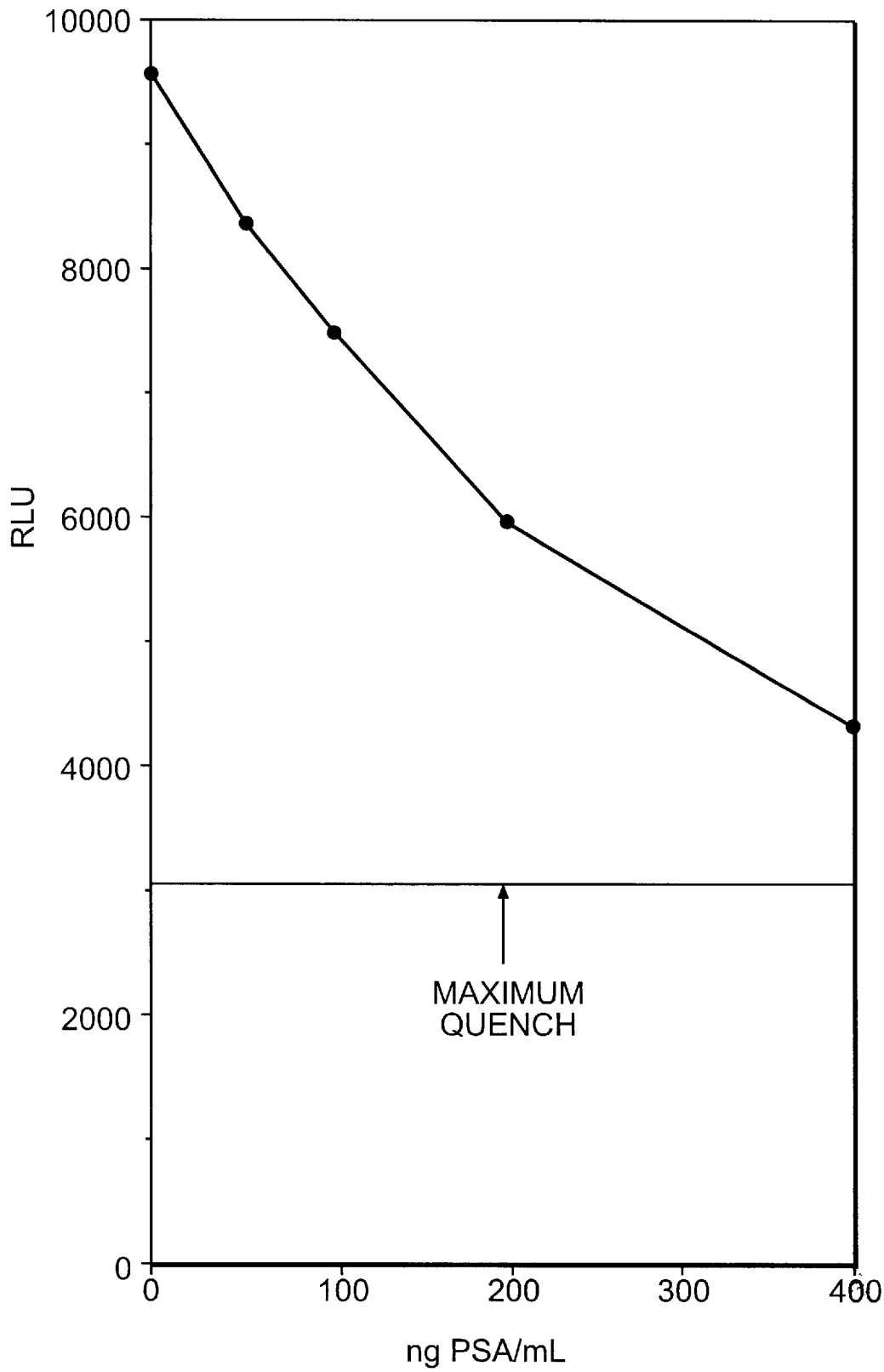
FIGS. 8 and 8a show a standard curve of LIA for determining PSA and a diagram of the method.
Figure 8A:
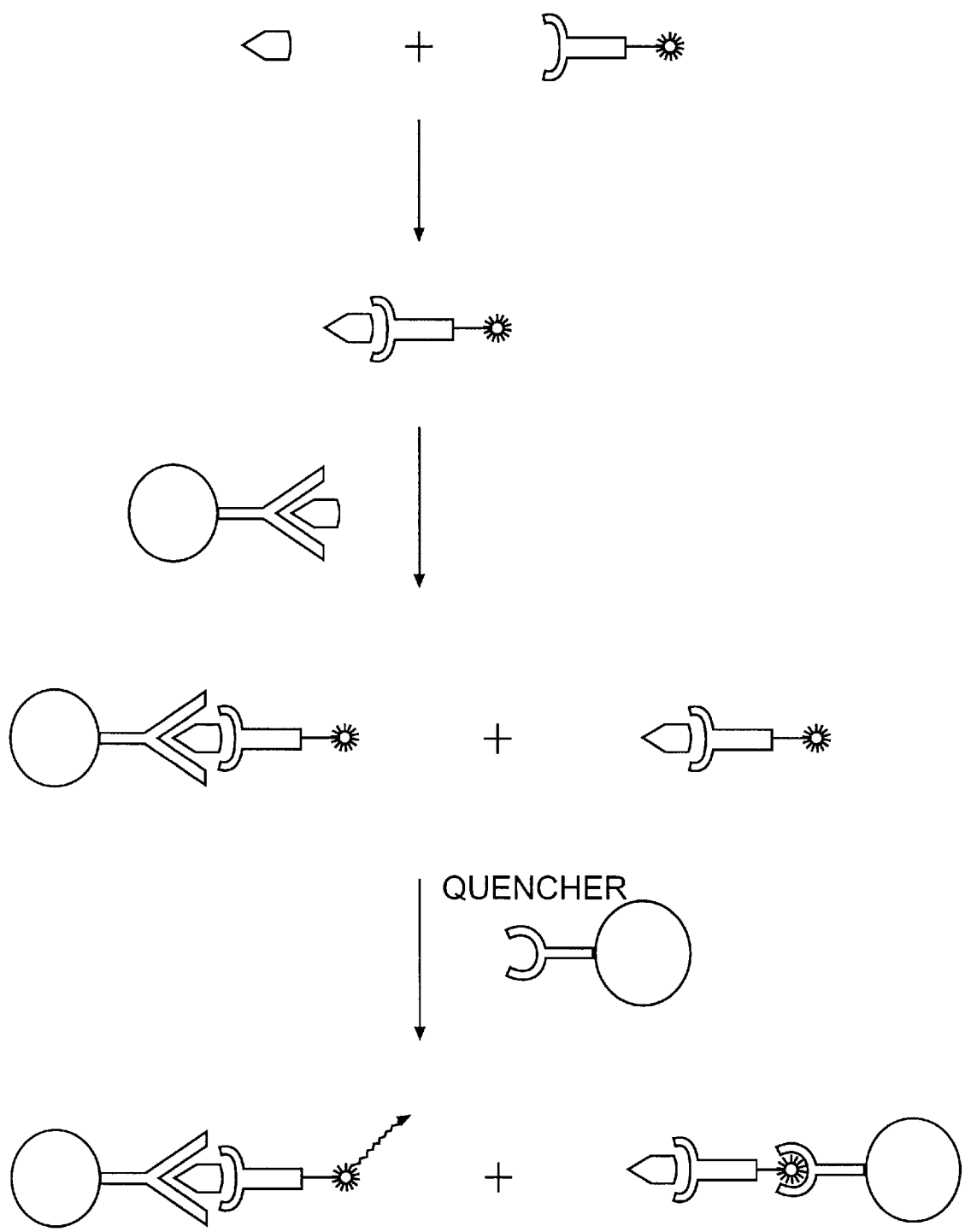

The results are depicted in FIG. 8 and the assay implementation is depicted schematically in FIG. 8a.

EXAMPLE 2

Immunoluminometric Assay (ILMA) for Determining PSA

Preparation of the Reagents:

Solid phase A:

Magnetic particles from Rhône-Poulenc (Catalog No. EM1-100/40) were coated with a monoclonal anti-PSA antibody (BW 92-283/029; Behringwerke AG, Marburg) using the carbodiimide method (G. Wendlberger et al., Synthese von Peptiden [Synthesis of peptides], Part II, Methoden Org. Chem. [Methods of organic chemistry] (Houben-Weyl) 4th ed. 1952, Vol. XV/2, 1974). The coating concentration was 6 mg of antibody per ml of 10% magnetic particle suspension. The ready-to-use suspension had a magnetic particle concentration of 10 mg/ml of storage buffer (50 mM CHES, 0.5 g of NaN$_3$/l, 3 g of bovine serum albumin/l, pH 8.0).

Solid phase B:

Magnetic particles were coated, as in the case of solid phase A, with a monoclonal antibody which is directed against the acridinium N-acylsulfonamide label (EP-A-0

257 541 and EP-A-0 330 050) (BW 90-9/04; Behringwerke AG; deposited in the Deutsche Sammlung von Mikroorganismen und Zellkulturen GmbH [German Collection of Microorganisms and Cell Cultures], Braunschweig, Germany, under deposition number DSM ACC 2184). The ready-to-use suspension had a magnetic particle concentration of 2.5 mg/ml of storage buffer (50 mM CHES, 0.5 g of $NaN_3$/l, 3 g of bovine serum albumin/l, pH 8.0).

Tracer:

A monoclonal anti-PSA antibody (BW 92-284/03, Behringwerke AG) was labeled with the acridinium-N-acylsulfonamide label (EP-A-0 257 541 and EP-A-0 330 050) in a molar ratio of 1+0.5. The labeling was carried out in accordance with the NHS method, which is described in the literature (NHS=N-hydroxysuccinimide reactive group; A. K. Campbell, Chemiluminescence: Principles and Applications in Biology and Medicine, 1st edition, VCH/Horwood, Weinheim/Chichester, 1988, p. 439). Gel permeation chromatography (Sephadex G 25) was used for the purification. The tracer was stored at a concentration of 30 mg/ml of tracer buffer (10 mM sodium acetate, 150 mM NaCl, 2 g of bovine serum albumin/l, 0.1% Mergal K9N, pH 5.0).

PSA standards:

The buffer in which PSA (prostate-specific antigen, Behringwerke AG) was dissolved had the following composition: 50 mM Tris, 150 mM NaCl, 0.05% $NaN_3$, 0.01% Tween 20, 0.5 g of bovine IgG/l, 40 g of bovine serum albumin/l, 8 mg of Titriplex V/l, pH 7.6. The standard concentrations were 0, 0.2, 0.4, 0.8, 1.6, 3.1, 6.2 and 12.5 mg/ml.

Assay Implementation:

10 ml of sample containing PSA were incubated at 37° C. for 20 minutes together with 10 ml of tracer and 10 ml of solid phase A. 10 ml of solid phase B were then added, and the mixture was measured for 1 s in a luminometer (BeriLux® analyzer) after a further 15 minutes.

Figure 9:
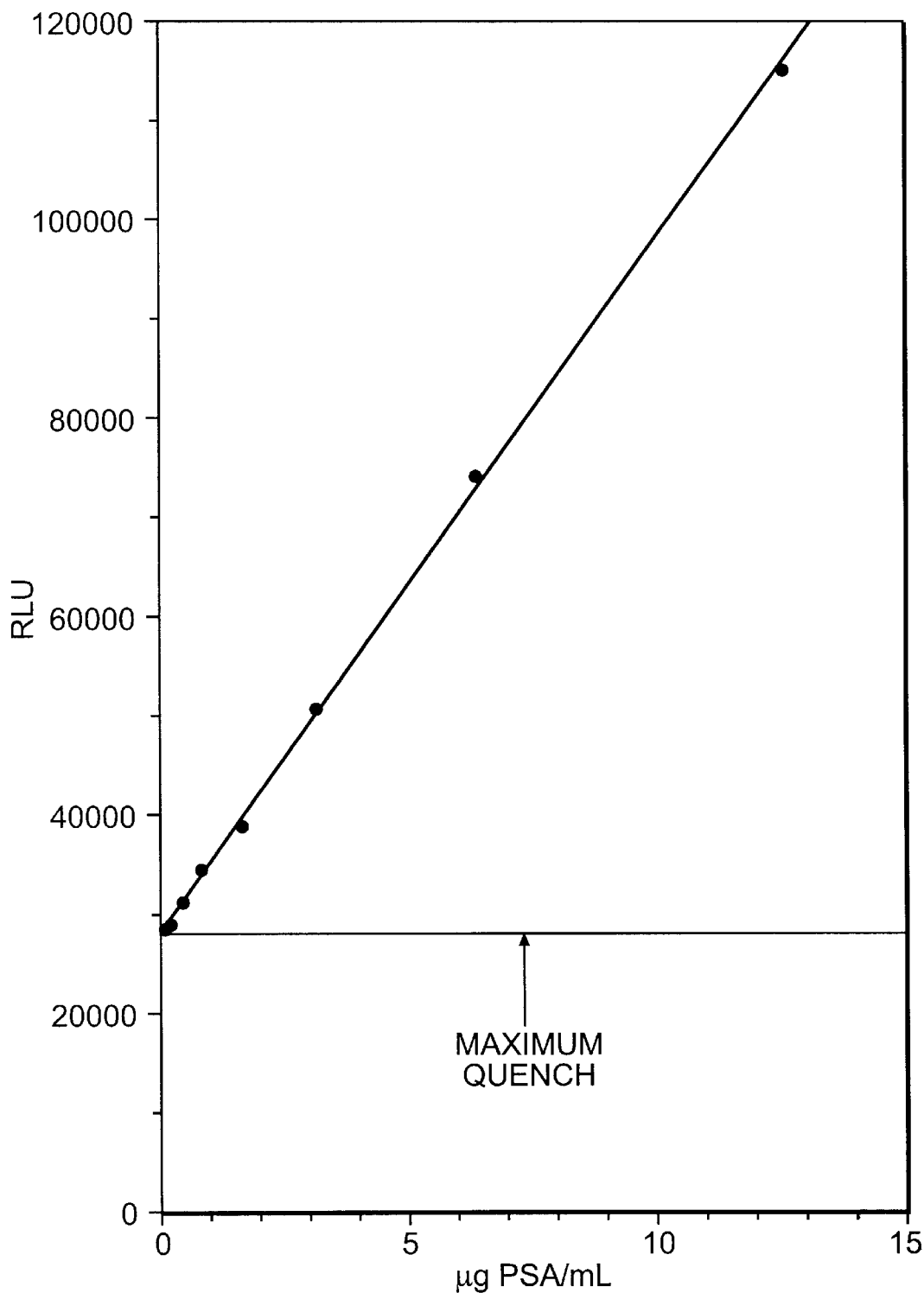
FIGS. 9 and 9a show a standard curve of ILMA for determining PSA and a diagram of the method.
Figure 9A:
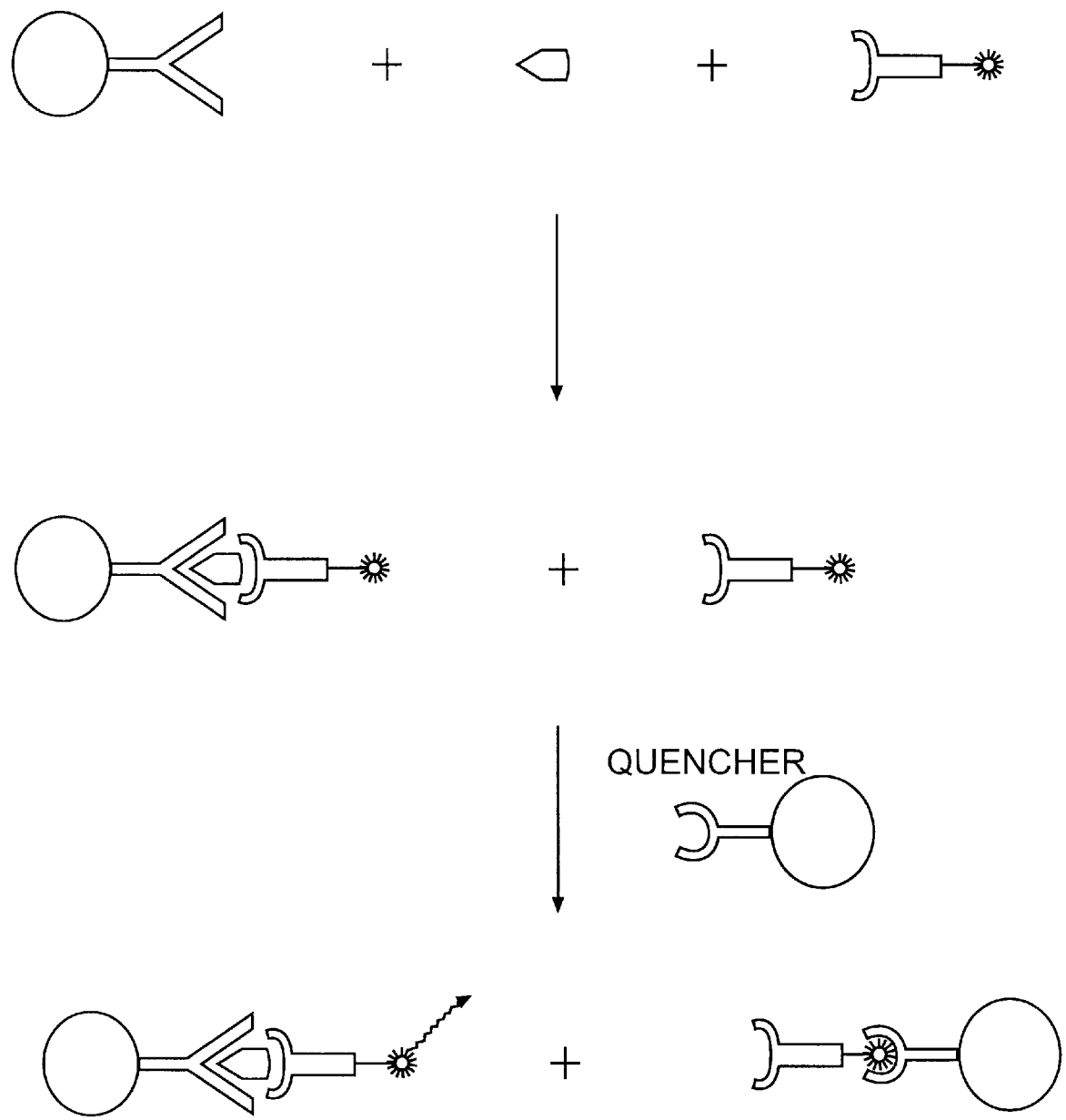

The results are depicted in FIG. 9 and the assay implementation is depicted schematically in FIG. 9a.

EXAMPLE 3

SPALT Assay for Determining Thyroxine

Preparation of the Reagents:

Solid phase A:

Magnetic particles from Rhône-Poulenc (Catalog No. EM1-100/20) were coated with the protein/T3 conjugate which is used in BeriLux T3 in accordance with the carbodiimide method [G. Wendlberger et al., Synthese von Peptiden [Synthesis of peptides], Part II, Methoden Org. Chem. [Methods of organic chemistry] (Houben-Weyl) 4th ed. 1952, Vol. XV/2, 1974]. The coating concentration was 0.3 mg of conjugate per ml of 10% magnetic particle suspension. The ready-to-use suspension had a magnetic particle concentration of 2.5 mg per ml of storage buffer (50 mM; Tris/citrate buffer, 0.5 g of $NaN_3$/l, 3 g of bovine serum albumin/l, pH 7.0).

Solid phase B:

Magnetic particles from Rhône-Poulenc (Catalog No. EM1-100/40) were coated with a monoclonal antibody, which is directed against the acridinium N-acylsulfonamide label (EP-A-0 257 541 and EP-A-0 330 050) (BW 90-8/04; Behringwerke AG; deposited in the Deutsche Sammlung von Mlkroorganismen und Zellkulturen GmbH, [German Collection of Microorganisms and Cell Cultures], Braunschweig, Germany, under deposition number DSM ACC 2184), in accordance with the carbodiimide method [G. Wendlberger et al., Synthese von Peptiden [Synthesis of peptides], Part II, Methoden Org. Chem. [Methods of organic chemistry] (Houben-Weyl) 4th ed. 1952, Vol. XV/2, 1974]. The coating concentration was 6 mg of antibody per ml of 10% magnetic particle suspension. The ready-to-use suspension had a magnetic particle concentration of 2.5 mg/ml of storage buffer (50 mM CHES, 0.5 g of $NaN_3$/l, 3 g of bovine serum albumin/l, pH 8.0).

Tracer:

A monoclonal anti-T4 antibody (BE 86-49/7/1, Behringwerke AG) was labeled with the acridinium N-acylsulfonamide label (EP-A-0 257 541 and EP-A-0 330 050) in a molar ratio of 1+5. The labeling was carried out using the NHS method, which is described in the literature (NHS=N-hydroxysuccinimide reactive group; A. K. Campbell, Chemiluminescence: Principles and Applications in Biology and Medicine, 1st edition, VCH/Horwood, Weinheim/Chichester, 1988, p. 439). Gel permeation chromatography (Sephadex G 25) was used for the purification. The tracer was stored at a concentration of 40 mg/ml of tracer buffer (50 mM citric acid/phosphate buffer, 2 g of polyethylene glycol 6000/l, 2 g of Mowiol/l; pH 6.3).

T4 standards:

The buffer for the T4 standards had the following composition: 10 mM phosphate, 1 g of bovine IgG/l, 0.5 g of $NaN_3$/l; pH 7.3. The standard concentrations were 0, 0.1, 0.5, 1, 5, 10 and 50 mg/ml.

Preformed complex:

The preformed complex (tracer bound to solid phase A) was prepared as follows:

6 ml of solid phase A were concentrated down to 3 ml (magnetic separation of the solid phase and resuspension in buffer). 0.2 ml of tracer was then added, and the mixture was incubated at. 37° C. for 30 minutes. The particles were washed 5' with 10 mM phosphate buffer, 1 g of IgG/l, 0.5 g of $NaN_3$/l, pH 7.3 (washing buffer). The particles were stored in 3 ml of washing buffer.

Assay Implementation:

10 ml of sample containing T4 were incubated at RT for 2 minutes with 10 ml of preformed complex. 10 ml of solid phase B were then added, and the mixture was measured for 1 s in a luminometer (BeriLux® analyzer) after a further 2 minutes.

Figure 10:
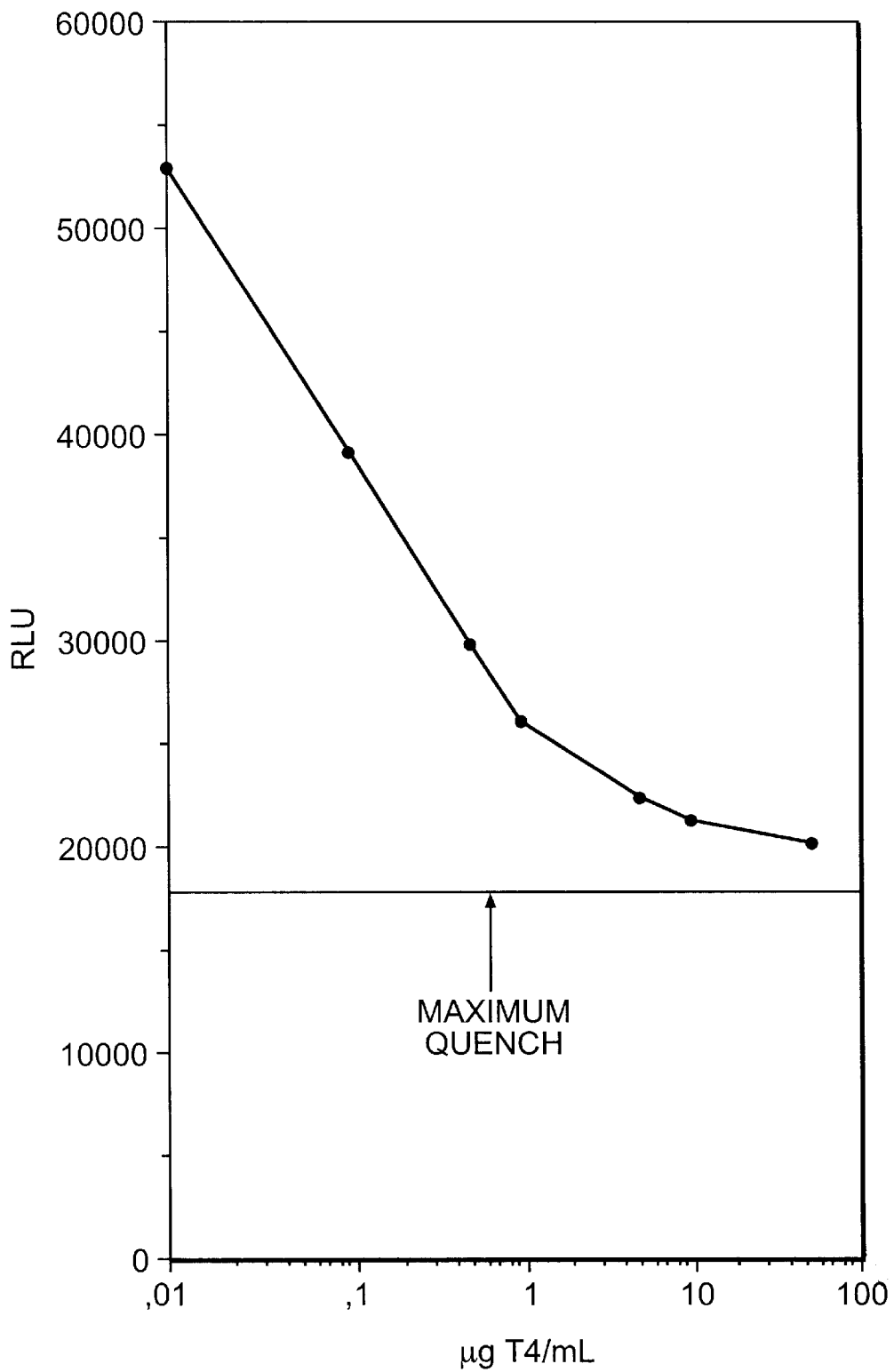
FIGS. 10 and 10a show a standard curve of SPALT assay for determining thyroxine and a diagram of the method.
Figure 10A:
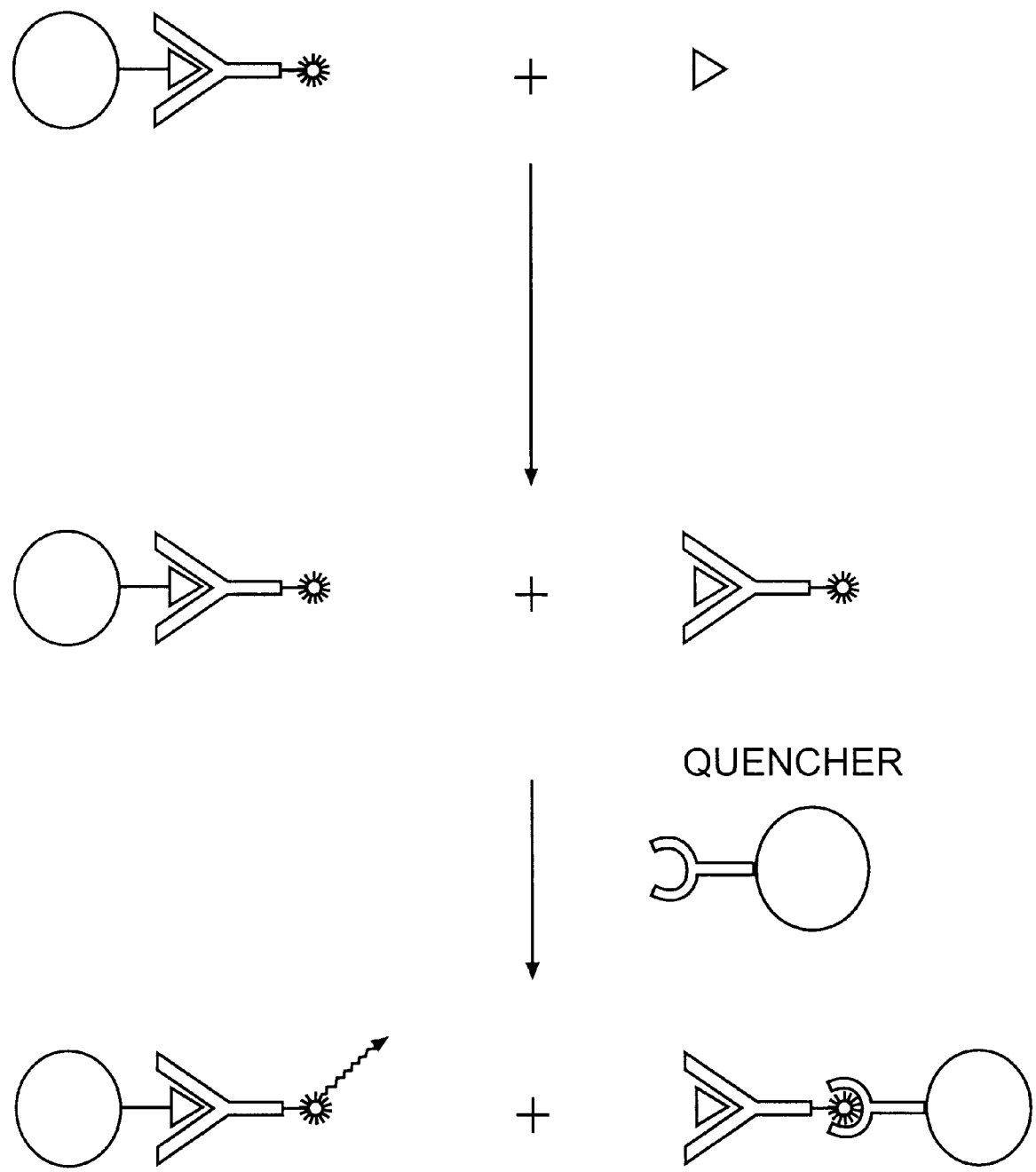

The results are depicted in FIG. 10 and the assay implementation is depicted schematically in FIG. 10a.

EXAMPLE 4

LIA for Determining Thyroxine (Protector/Quencher Method)

Preparation of the Reagents:

Solid phase A:

Magnetic particles from Rhône-Poulenc (Catalog No. EM1-100/20) were coated with a monoclonal anti-T4 antibody (BW 86-49/7/1, Behringwerke AG) in accordance with the carbodiimide method (G. Wendlberger et al., Synthese von Peptiden [Synthesis of peptides], Part II, Methoden Org. Chem. [Methods of organic chemistry, (Houben-Weyl) 4th ed. 1952, Vol. XV/2, 1974). The coating concentration was 1.2 mg of antibody/ml of 10% magnetic particle suspension. The ready-to-use suspension had a magnetic particle concentration of 2.5 mg/ml of storage buffer (10.36 g of CHES, 0.5 g of sodium azide, 1 g of bovine IgG/l, pH 8.0).

Solid phase B:

Magnetic particles from Rhône-Poulenc (Catalog No. EM1-100/40) were coated with a monoclonal antibody which is directed against the acridinium N-acylsulfonamide label (EP-A-0 257 541 and ]EP-A-0 330 050) (protector antibody, BW 90-9/016; Behringwerke AG; deposited in the Deutsche Sammlung von Mikrcorganismen und Zellkulturen GmbH, [German Collection of Microorganisms and Cell Cultures], Braunschweig, Germany, under deposition number DSM ACC 2183) in accordance with the carbodiimide method (G. Wendlberger et al., Synthese von Peptiden [Synthesis of Peptides], Part II, Methoden Org. Chem. [Methods of Organic Chemistry] (Houben-Weyl) 4th ed. 1952, Tol. XV/2, 1974). The coating concentration was 6 mg of antibody/ml of 10% magnetic particle suspension. The ready-to-use suspension had a magnetic particle concentration of 2.5 mg/ml of storage buffer (10.36 g of CHES, 0.5 g of sodium azide, 3 g of bovine serum albumin/l, pH 8.0).

Tracer:

The tracer used in the BeriLux FT3 was stored at a concentration of 360 ng/ml of tracer buffer (10 mM phosphate buffer, 1 g of IgG/l, pH 7.3).

Ouencher antibody:

The anti-label antibody BW 90-8/04 (Behringwerke AG deposited in the Deutsche Sammlung von Mikroorganismen und Zellkulturen GmbH, [German Collection of Microorganisms and Cell Cultures], Braunschweig, Germany, under deposition number DSM ACC 2184) was stored at a concentration of 0.1 mg/ml of buffer (10 mM phosphate, 1 g of IgG/l, 0.5 g of sodium azide/l, pH 7.3).

T4 standards:

BeriLux® T4 standards (Behringwerke AG) having a concentration of 0; 18; 40; 85; 175 and 340 ng/ml of serum medium were employed.

Preformed complex:

The preformed complex (tracer bound to solid phase A) was prepared as follows:

2 ml of tracer were added to 2 ml of solid phase A, and the mixture was incubated at 37° C. for 30 minutes. The particles were washed 5' with 10 mM phosphate buffer, 1 g of IgG/l, 0.5 g of sodium azide/l, pH 7.3, and were made up to 2 ml. 2 mg of ANS (8-anilinonaphthalene-1-sulfonic acid) were then added.

Assay implementation:

10 ml of preformed complex and 10 ml of sample containing T4 were incubated for 15 minutes. 10 ml of solid phase B and 10 ml of quencher antibody were subsequently added at intervals of in each case 10 minutes, and the suspension was measured for 1 s in a luminometer (BeriLux® analyzer).

A constant incubation temperature of 37° C. was maintained.

Figure 11:
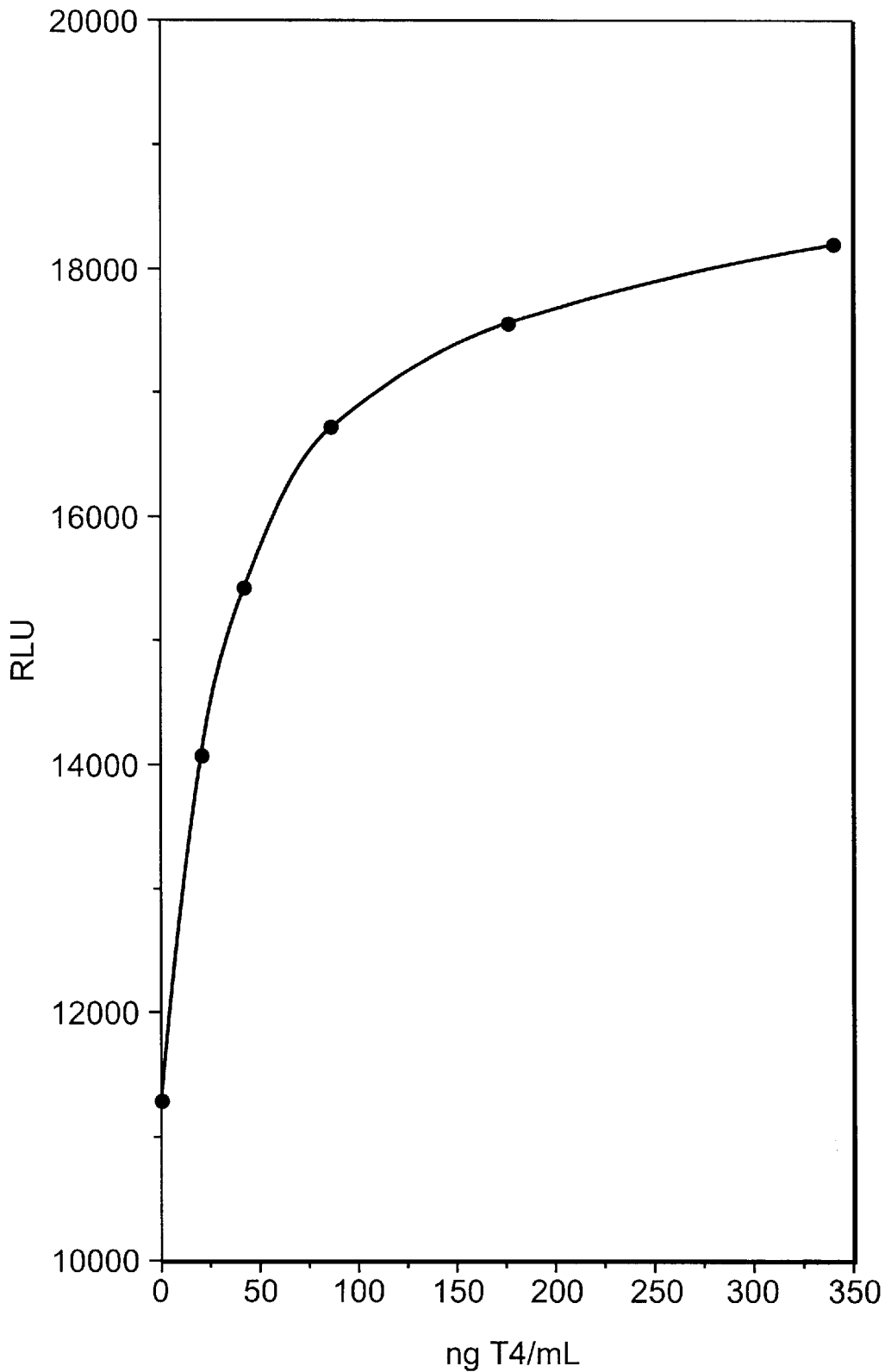
FIGS. 11 and 11a show a standard curve of LIA, for determining thyroxine and a diagram of the method.
Figure 11A:
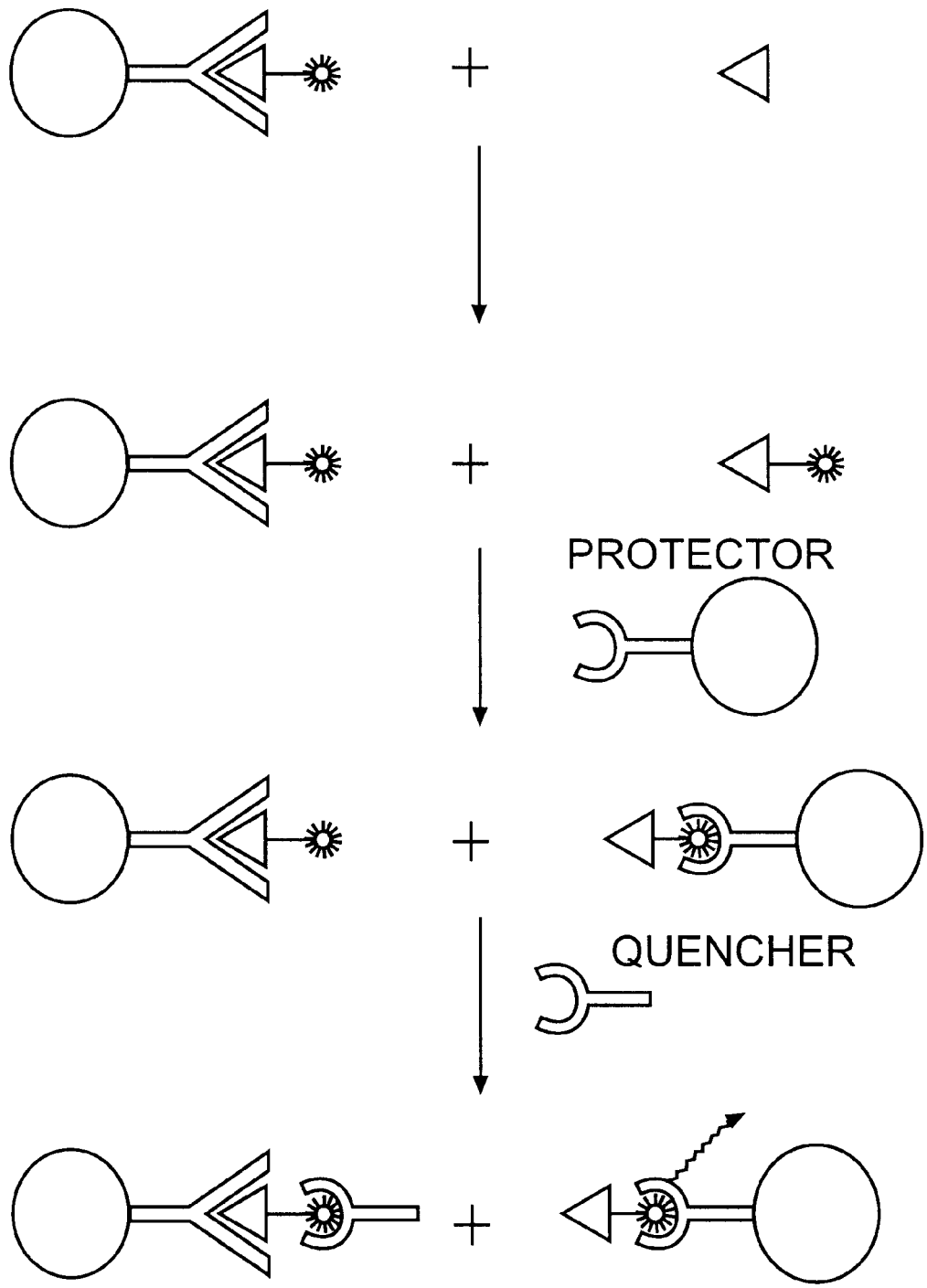

The results are depicted in FIG. 11 and the assay implementation is depicted schematically in FIG. 11a.

EXAMPLE 5

LIA for Determining Thyroxine

Preparation of the Reagents:

Solid phase A:

Magnetic particles from Rhône-Poulenc (Catalog No. EM1-100/20) were coated with a monoclonal anti-T4 antibody (BW 86-49/7/1, Behringwerke AG) in accordance with the carboduimide method (G. Wendlberger et al., Synthese von Peptiden, [Synthesis of peptides], Part II, Methoden Org. Chem. [Methods of organic chemistry], (Houben-Weyl) 4th ed. 1952, Vol. XV/2, 1974). The coating concentration was 1.25 mg of antibody/ml of 10% magnetic particle suspension. The ready-to-use suspension had a magnetic particle concentration of 2.5 mg/ml of storage buffer (10.36 g of CHES, 0.5 g of sodium azide, 1 g of bovine IgG/l, pH 8.0).

Solid phase B:

Magnetic particles from Rhône-Poulenc (Catalog No. EM1-100/40) were coated with a monoclonal antibody which is directed against the BeriLux label (Quencher antibody EW 90-8/04; Behringwerke AG; deposited in the Deutsche Sammlung von Mikroorganismen und Zellkulturen GmbH, [German Collection of Microorganisms and Cell Cultures], Braunschweig, Germany, under deposition number DSM ACC 2184) in accordance with the carbodiimide method (G. Wendlberger et al., Synthese von Peptiden [Synthesis of peptides], part II, Methoden Org. Chem. [Methods of organic chemistry] (Houben-Weyl) 4th ed. 1952, Vol. XV/2, 1974). The coating concentration was 6 mg of antibody/ml of 10% magnetic particle suspension. The ready-to-use suspension had a magnetic particle concentration of 2.5 mg/ml of storage buffer (10.36 g of CHES, 0.5 g of sodium azide, 3 g of bovine serum albumin/l, pH 8.0).

Tracer:

The tracer used in the BeriLux FT3 was stored at a concentration of 360 ng/ml of tracer buffer (10 mM phosphate buffer, 1 g of IgG/l, 0.5 g of $NaN_3$/l, pH 7.3).

T4 Standards:

BeriLux® T4 standards (Behringwerke AG) having a concentration of 0; 18; 40; 85; 175 and 340 ng/ml of serum medium were employed.

Preformed complex:

The preformed complex (tracer bound to solid phase A) was prepared as follows:

2 ml of tracer were added to 2 ml of solid phase A, and the mixture was incubated at 37° C. for 30 minutes. The particles were washed 5× with 10 mM phosphate buffer, 1 g of IgG/l, 0.5 g of sodium azide/l, pH 7.3, and were made up to 2 ml. 2 mg of ANS (8-anilinonaphthalene-1-sulfonic acid) were then added.

Assay implementation:

10 μl of preformed complex and 10 μl of sample containing T4 were incubated for 15 minutes. 10 μl of solid phase B were subsequently added and the mixture was incubated for a further 10 minutes before the suspension was measured for 1 s in a luminometer (BeriLux® analyzer).

A constant incubation temperature of 37° C. was maintained.

Figure 12:
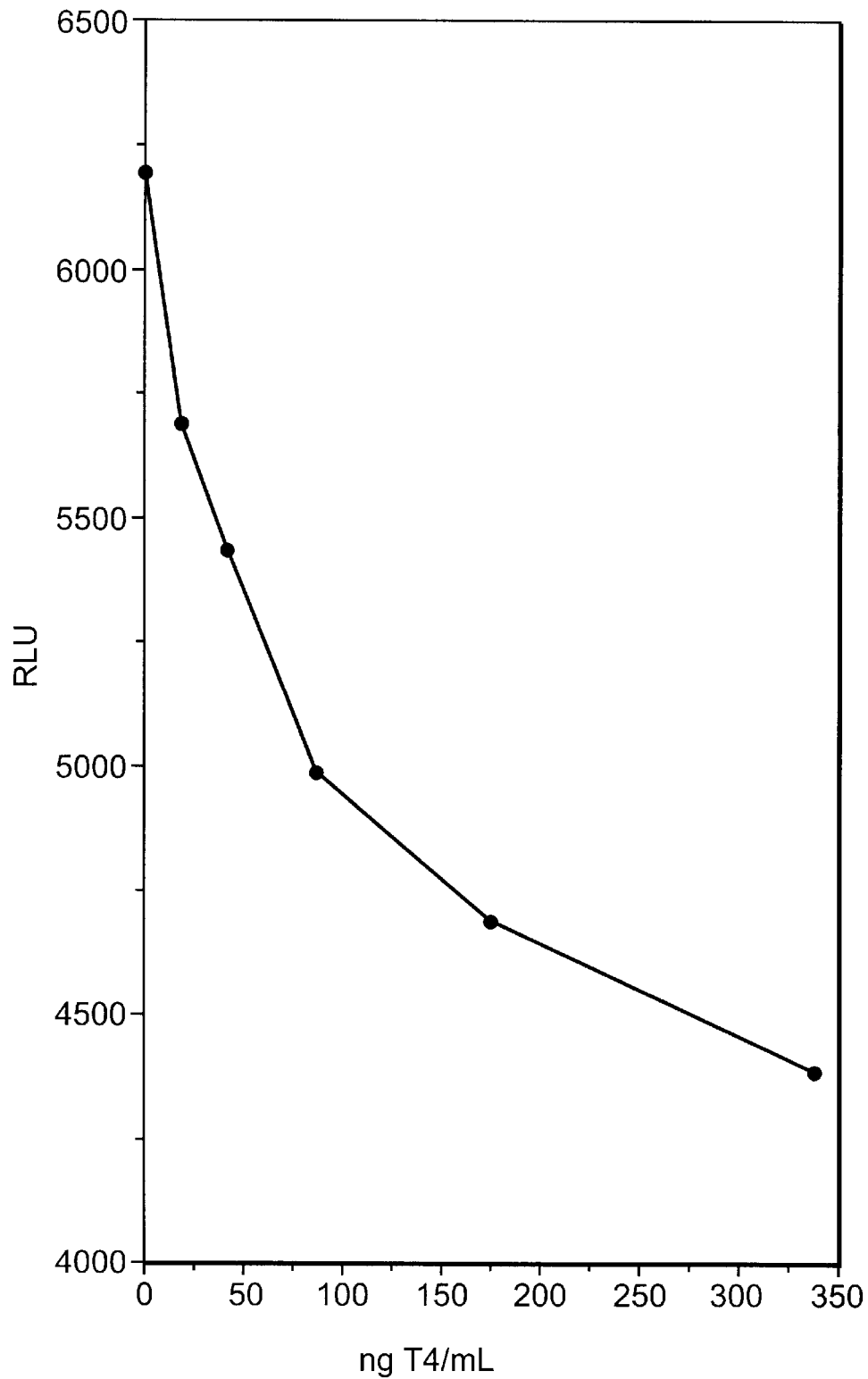
FIGS. 12 and 12a show a standard curve of a variation of LIA for determining thyroxine and a diagram of the method.
Figure 12A:
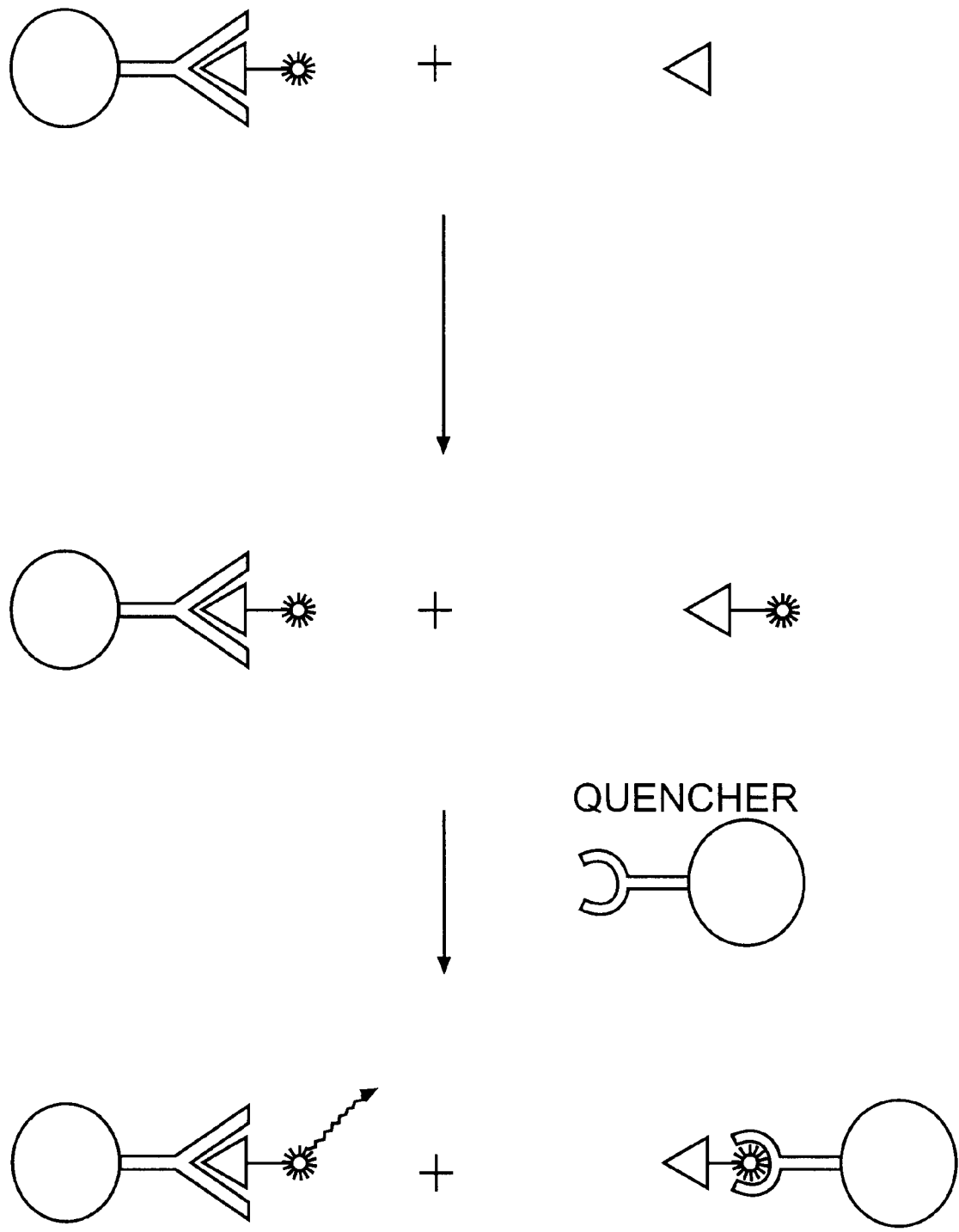

The results are depicted in FIG. 12 and the assay implementation is depicted schematically in FIG. 12a.

EXAMPLE 6

LIA for Determining FT3

Preparation of the Reagents:

Solid phase A:

Magnetic particles from Rhône-Poulenc (Catalog No. EM1-100/20) were coated with a monoclonal anti-T3 antibody (BeriLux FT3 antibody) in accordance with the carbodiimide method (G. Wendlberger et al., Synthese von Peptiden, [Synthesis of peptides], Part II, Methoden Org. Chem. [Methods of organic chemistry], (Houben-Weyl) 4th ed. 1952, Vol. XV/2, 1974). The coating concentration was 0.25 mg of antibody/ml of 10% magnetic particle suspension. The ready-to-use suspension had a magnetic particle concentration of 2.5 mg/ml of storage buffer (10.36 g of CHES, 0.5 g of sodium azide, 1 g of bovine IgG/l, pH 8.0).

Solid phase B:

Magnetic particles from Rhône-Poulenc (Catalog No. EM1-100/40) were coated with a monoclonal antibody which is directed against the BeriLux label (Quencher antibody BW 90-8/04; Behringwerke AG; deposited in the Deutsche Sammlung von Mikroorganismen und Zellkulturen GmbH, [German Collection of Microorganisms and Cell Cultures], Braunschweig, Germany, under deposition number DSM ACC 2184) in accordance with the carbodiimide method (G. Wendlberger et al., Synthese von Peptiden

[Synthesis of peptides], part II, Methoden Org. Chem. [Methods of organic chemistry] (Houben-Weyl) 4th ed. 1952, Vol. XV/2, 1974). The coating concentration was 6 mg of antibody/ml of 10% magnetic particle suspension. The ready-to-use suspension had a magnetic particle concentration of 2.5 mg/ml of storage buffer (10.36 g of CHES, 0.5 g of sodium azide, 3 g of bovine serum albumin/l, pH 8.0).

Figure 17:
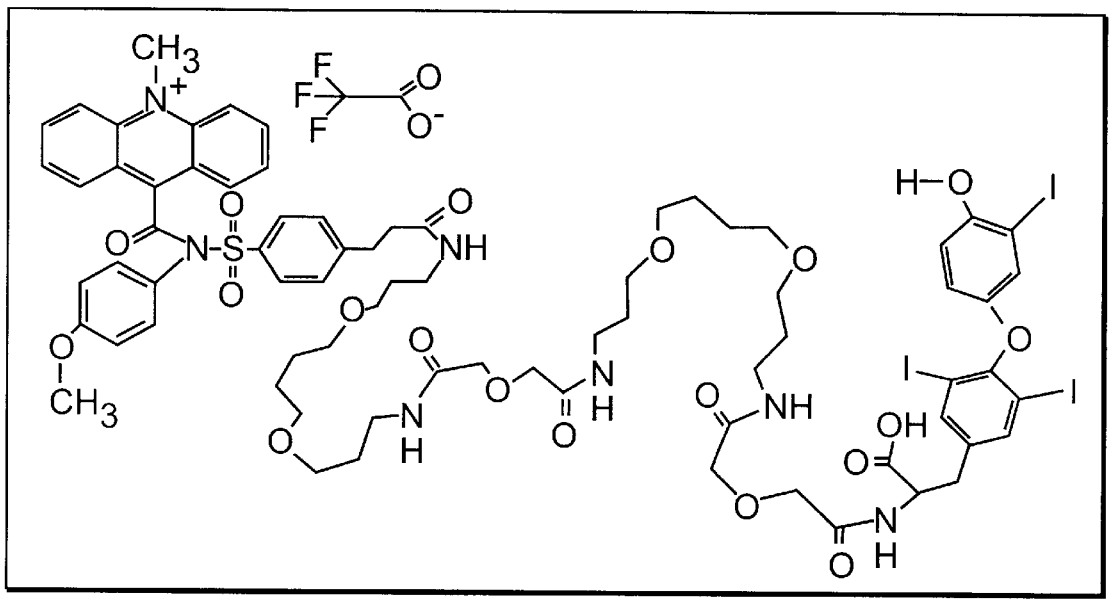
FIG. 17 shows the structure of $[C_{74}H_{88}I_3N_7O_{19}S]^+$ $[OF_3CO_2]^-$.
Figure 18:
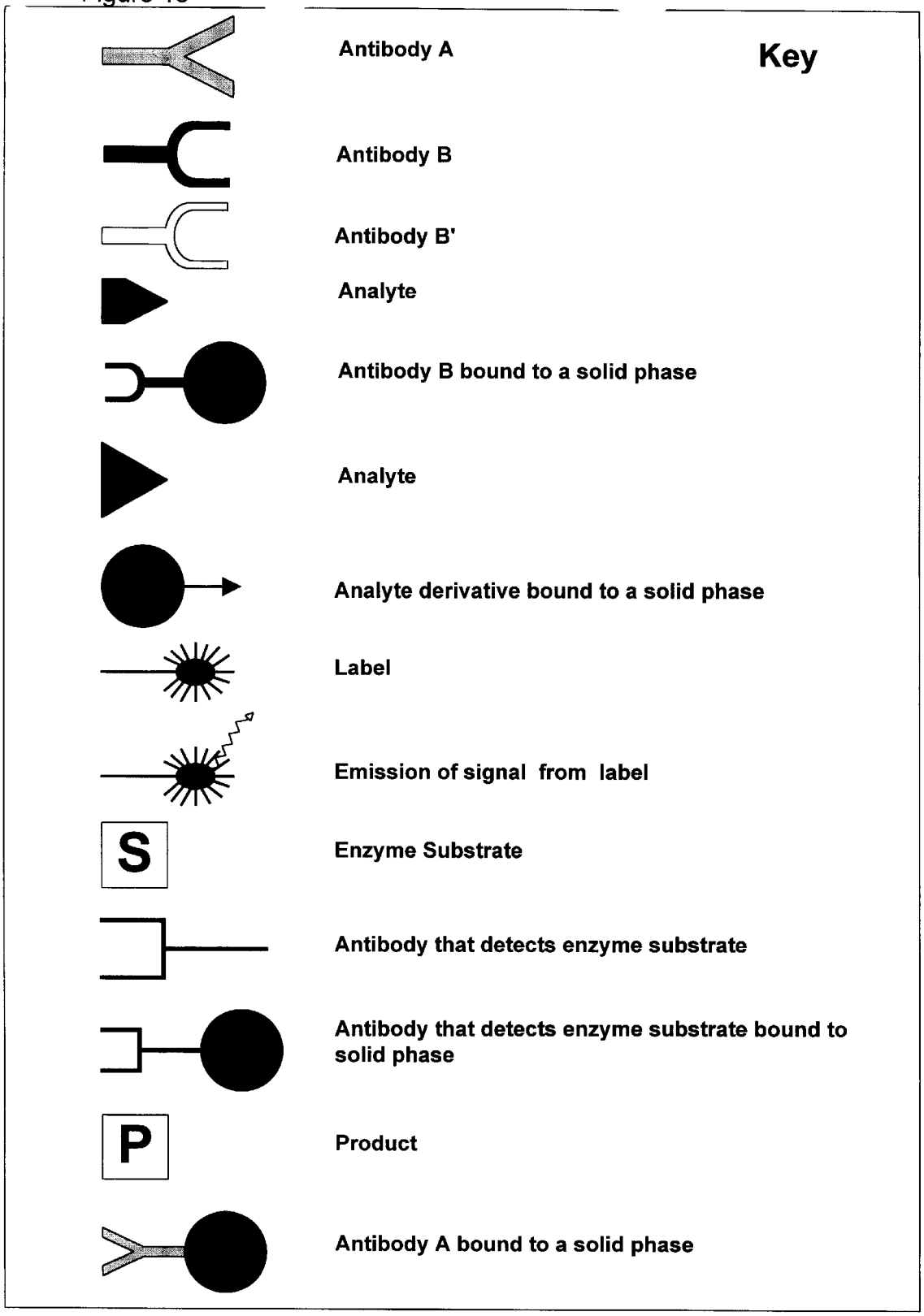
FIG. 18 is a key for the figures.

Tracer:

1 ng of hapten tracer (T3-acridinium tracer; see FIG. 17)/ml of tracer buffer (50 mM Tris/HCl; 150 mM NaCl; 0.5 mg of sodium azide/l; 0.1 g of Tween 20/l; 0.5 g of bovine IgG/l; 40 g of bovine serum albumin/l; 8 mg of Titriplex V/l; pH 7.6).

FT3 Standards:

FT3 standards in a concentration range of from 0 to 22 pg/ml were employed in a serum medium.

Assay Implementation: 50 μl of sample were incubated for 15 minutes together with 10 μl of tracer and 10 μl of solid phase A. 10 μl of solid phase B were subsequently added and the mixture was incubated for a further 10 minutes before measuring the suspension for 1 s in a luminometer (BeriLux® analyzer). A constant incubation Temperature of 37° C. was maintained.

Figure 13:
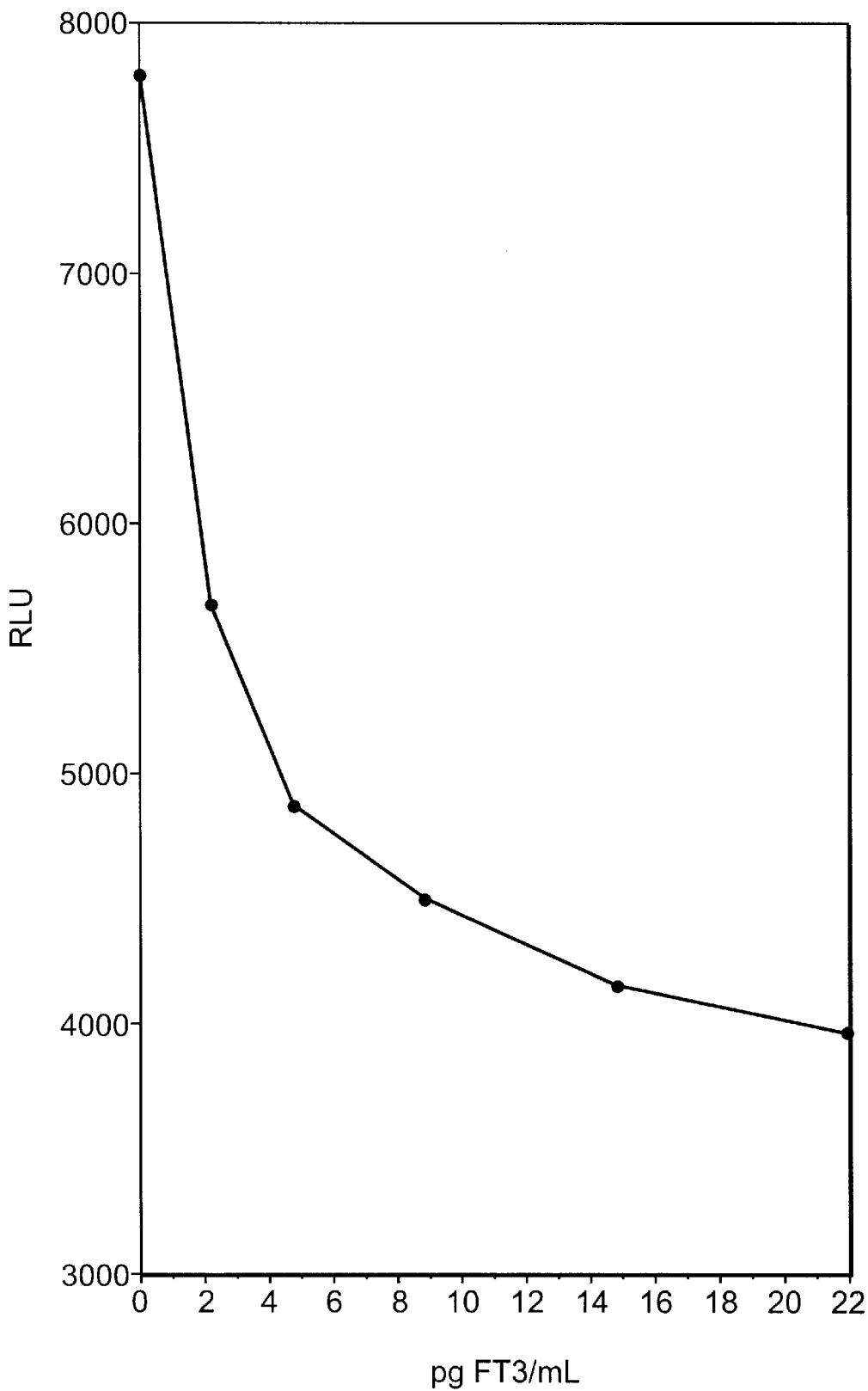
FIGS. 13 and 13a show a standard curve of LIA for determining FT3 and a diagram of the method.

The results are depicted in FIG. 13, and the assay implementation is depicted schematically in FIG. 3a.

EXAMPLE 7

Immunoluminometric Assay (ILMA) for Determining PSA

Preparation of the Reagents:

Solid chase A:

Magnetic particles from Rhône-Poulenc (Catalog No. EM1-100/40) were coated with a monoclonal anti-PSA antibody (BW 92-283/029; Behringwerke AG, Marburg) in accordance with the carbodiimide method (G. Wendlberger, P. Stelzel, Synthese von Peptiden, [Synthesis of peptides], Part II, Methoden Org. Chem. [Methods of organic chemistry] (Houben-Weyl) 4th ed. 1952, Vol. XV/2, 1974). The coating concentration was 6 mg of antibody/ml of 10% magnetic particle suspension. The ready-to-use suspension had a magnetic particle concentration of 10 mg/ml of storage buffer (50 mM CHES, 0.5 g of NaN$_3$/l, 3 g of bovine serum albumin/l, pH 8.0).

Solid phase B:

Magnetic particles were, as in the case of solid phase A, coated with a monoclonal antibody which is directed against the BeriLux label (BW 90-8/04; Behringwerke AG; deposited in the Deutsche Sammlung von Mikroorganismen und Zellkulturen GmbH, [German Collection of Microorganisms and Cell Cultures], Braunschweig, Germany, under deposition number DSM ACC 2184) The ready-to-use suspension had a magnetic particle concentration of 5 mg/ml of storage buffer (50 mM CHES, 0.5 g of NaN$_3$/l, 3 g of bovine serum albumin/l, pH 8.0).

Tracer concentrate:

A monoclonal anti-PSA antibody (BW 92-284/03, Behringwerke AG) was labeled with the BeriLux® label in a molar ratio of 1+10. The labeling was carried out using the NHS method which is described in the literature (NHS=N-hydroxysuccinimide reactive group; A. K. Campbell, Chemiluminescence: Principles and Applications in Biology and Medicine, 1st edition, VCH/Horwood, Weinheim/Chichester, 1988, p. 439). Purification was effected by means of gel permeation chromatography (Sephadex G 25). The tracer was stored at a concentration of 30 μg/ml of tracer buffer (10 mM sodium acetate, 150 mM NaCl, 2 g of bovine serum albumin/l, 0.1% Mergal K9N, pH 5.0).

Tracer:

In order to prepare the ready-to-use tracer, the tracer concentrate is diluted, in a ratio of 1:200, with 0.1 M phosphate buffer (pH 6.3 containing 0.15 NaCl and 1 g of bovine serum albumin per liter).

PSA Standards:

The buffer in which the PSA (prostate-specific antigen, Behringwerke AG) was dissolved had the following composition: 50 mM Tris, 150 mM NaCl, 0.05% NaN$_3$, 0.01% Tween 20, 0.5 g of bovine IgG/l, 40 g of bovine serum albumin/l, 8 mg of Titriplex V/l, pH 7.6. The standard concentrations were 0, 0.5, 3.2, 10.6, 32, 80 and 160 ng/ml.

Assay Implementation: 10 μl of PSA-containing sample were incubated at 37° C. for 15 minutes together with 10 μl of solid phase A and 20 μl of tracer. 10 μl of solid phase B were subsequently added and, after a further 5 minutes, the mixture was measured for 0.7 s in a luminometer (BeriLux® analyzer). 20 mM HNO$_3$ containing 0.5% H$_2$O$_2$ and 125 mM NaOH were used as light emitting reagents.

Figure 14:
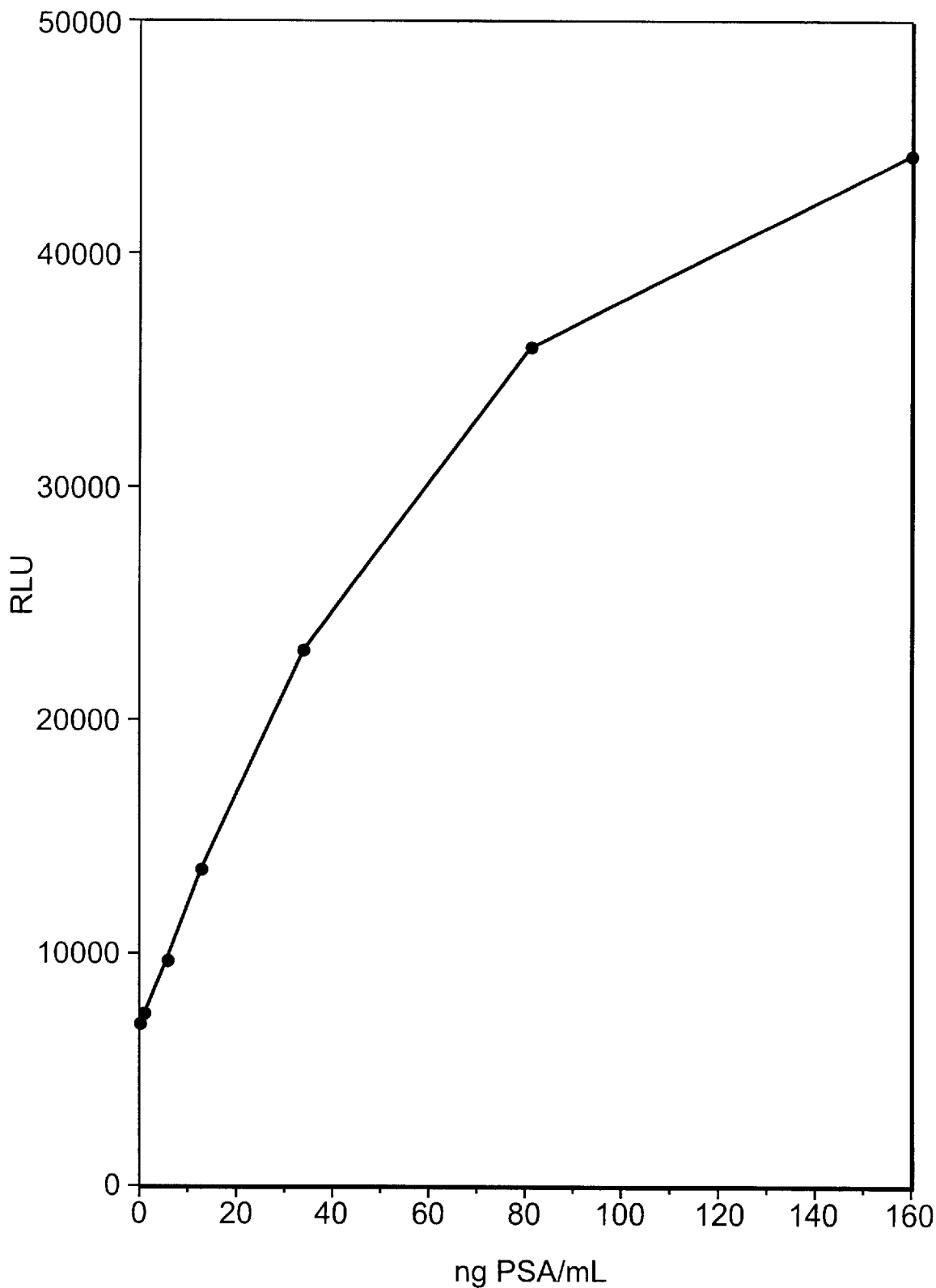
FIG. 14 shows a standard curve of an ILMA for determining PSA.

The results are depicted in FIG. 14, and the assay implementation is depicted schematically in FIG. 9a.

EXAMPLE 8

Irnmunoluminometric Assay (ILMA) for Determining PSA

Preparation of the Reagents:

Solid phase A:

Magnetic particles from Rhône-Poulenc (Catalog No. EM1-100/40) were coated with a monoclonal anti-ISA antibody (BW 92-283/029; Behringwerke AG, Marburg) in accordance with the carbodiimide method (G. Wendlberger, P. Stelzel, Synthese von Peptiden, [Synthesis of peptides], Part II, Methoden Org. Chem. [Methods of organic Chemistry] (Houben-Weyl) 4th ed. 1952, Vol. XV/2, 1974). The coating concentration was 6 mg of antibody/ml of 10% magnetic particle suspension. The ready-to-use suspension had a magnetic particle concentration of 10 mg/ml of storage buffer (50 mM CHES, 0.5 g of NaN$_3$/l, 3 g of bovine serum albumin/l, pH 8.0).

Solid phase BB:

Magnetic particles were, as in the case of solid phase A, coated with a monoclonal antibody which is directed against the BeriLux label (BW 90-8/04; Behringwerke AG; deposited in the Deutsche Sammlung von Mikroorganismen und Zellkulturen GmbH, [German Collection of Microorganisms and Cell Cultures], Braunschweig, Germany, under deposition number DSM ACC 2184). The ready-to-use suspension had a magnetic particle concentration of 5 mg/ml of storage buffer (50 mM CHES, 0.5 g of NaN$_3$/l, 3 g of bovine serum albumin/l, pH 8.0).

Tracer concentrate:

A monoclonal anti-PSA antibody (BW 92-284/03, Behringwerke AG) was labeled with the BeriLux® label in a molar ratio of 1+10. The labeling was carried out using the NHS method which is described in the literature (NHS=N-hydroxysuccinimide reactive group; A. K. Campbell, Chemiluminescence: Principles and Applications in Biology and Medicine, 1st edition, VCH/Horwood, Weinheim/Chichester, 1988, p. 439). Purification was effected by means of gel permeation chromatography (Sephadex G 25). The tracer was stored at a concentration of 30 μg/ml of tracer buffer (10 mM sodium acetate, 150 mM NaCl, 2 g of bovine serum albumin/l, 0.1% Mergal K9N, pH 5.0).

Tracer:

In order to prepare the ready-to-use tracer, the tracer concentrate is diluted, in a ratio of 1:200, with 0.1 M phosphate buffer (pH 6.3 containing 0.15 NaCl and 1 g of bovine serum albumin per liter).

Measuring buffer:

12.1 g of tris(hydroxymethyl)aminomethane, 8.8 g of sodium chloride, 0.1 g of sodium azide and 10 g of Tween 20 are dissolved in 990 ml of deionized water, and this solution is adjusted to pH 8.0 with 25% hydrochloric acid.

Medium effects can be reduced by employing the measuring buffer in combination with suitable lightemitting reagents (see assay implementation).

PSA Standards:

The buffer in which PSA (prostate-specific antigen, Behringwerke AG) was dissolved had the following composition: 50 mM Tris, 150 mM NaCl, 0.05% $NaN_3$, 0.01% Tween 20, 0.5 g of bovine IgG/l, 40 g of bovine serum albumin/l and 8 mg of Titriplex V/l, pH 7.6. The standard concentrations were 0, 3.2, 10.6, 32, 80 and 160 ng/ml.

Assay Implementation:

10 µl of PSA-containing sample were incubated at 37° C. for 15 minutes together with 10 µl of solid phase A and 20 µl of tracer. 10 µl of solid phase B were subsequently added, as were 200 µl of measuring buffer after a further 5 minutes. The mixture was measured for 0.7 s in a luminometer (BeriLux® analyzer) 20 mM $HNO_3$ containing 0.5% $H_2O_2$ and 125 mM NaOH were used as light-emitting reagents.

Figure 15:
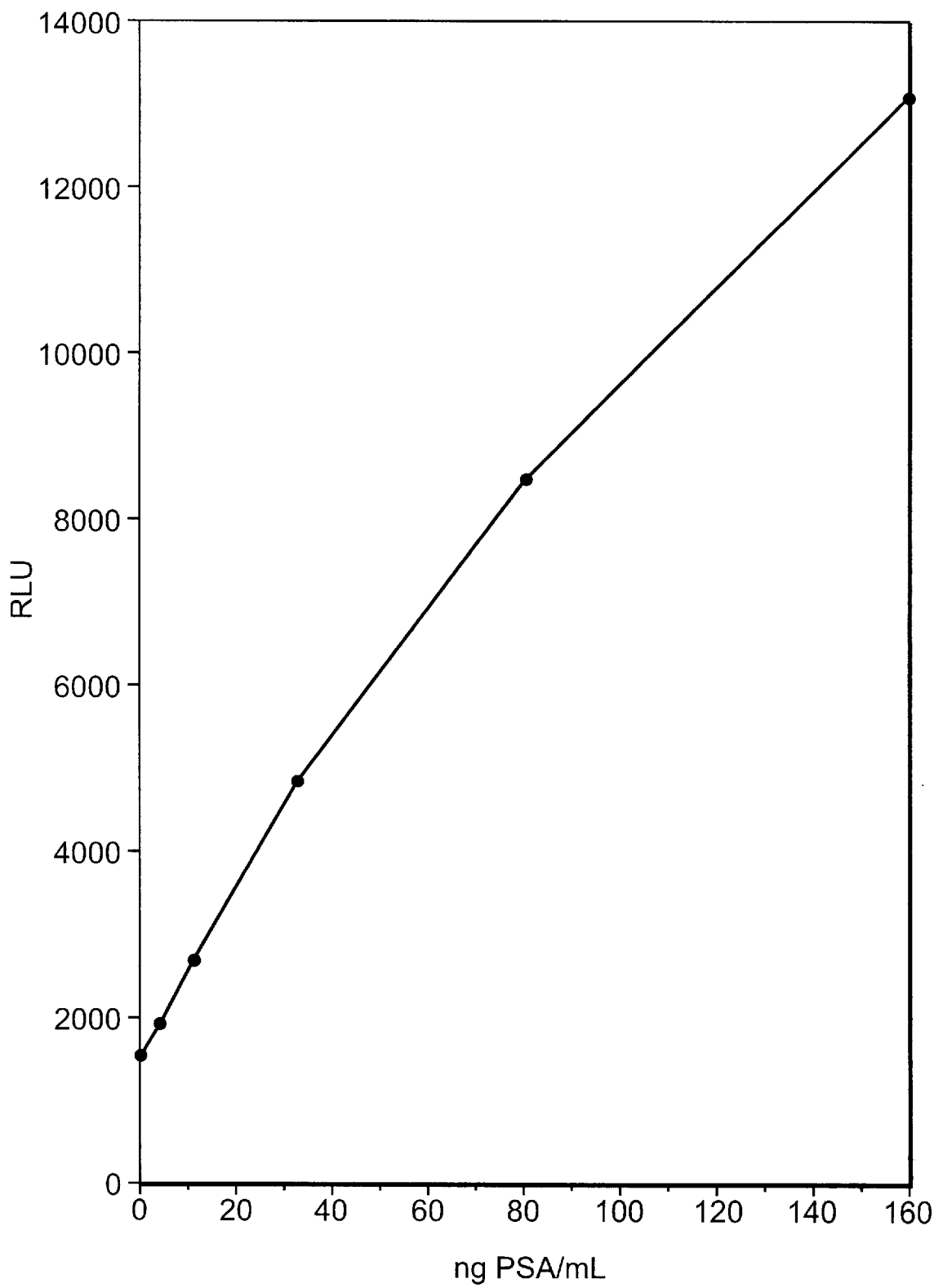
FIG. 15 shows a standard curve of an ILMA for determining PSA.

The results are depicted in FIG. 15, and the assay implementation is depicted schematically in FIG. 9a.

EXAMPLE 9

LIA for Determining T3

Preparation of the Reagents:

Solid phase A:

Magnetic particles from Rhône-Poulenc (Catalog No. EM1-100/20) were coated with a monoclonal anti-T3 antibody (BeriLux FT3-antibody) in accordance with the carbodiimide method [G. Wendlberger, P. Stelzel, Synthese von Peptiden, [Synthesis of peprides], Part II, Methoden Org. Chem. [Methods of organic chemistry] (Houben-Weyl) 4th ed. 1952, Vol. XV/2, 1974]. The coating concentration was 0.25 mg of antibody/ml of 10% magnetic particle suspension. The ready-to-use suspension had a magnetic particle concentration of 2.5 mg/ml of storage buffer (10.36 g of CHES, 0.5 g of sodium azide, 3 g of bovine serum albumin/l, pH 8.0).

Solid phase B:

Magnetic particles from Rhône-Poulenc (Catalog No. EM1-100/60) were coated with a monoclonal antibody which is directed against the BeriLux label (Quencher antibody BW 90-8/04; Behringwerke AG; deposited in the Deutsche Sammlung von Mikroorganismen und Zellkulturen GmbH, [German Collection of Microorganisms and Cell Cultures], Braunschweig, Germany, under deposition number DSM ACC 2184) in accordance with the carbodiimide method (G. Wendlberger et al., Synthese von Peptiden [Synthesis of peptides], part II, Methoden Org. Chem. [Methods of organic chemistry] (Houben-Weyl) 4th ed. 1952, Vol. XV/2, 1974). The coating concentration was 6 mg of antibody/ml of 10% magnetic particle suspension. The ready-to-use suspension had a magnetic particle concentration of 2.5 mg/ml of storage buffer (10.36 g of CHES, 0.5 g of sodium azide, 3 g of bovine serum albumin per liter, pH 8.0).

Synthesis of the Tracer

Step 1: Preparation of a streptavidin-T3 conjugate a) 3 mg of streptavidin are dissolved in 1.7 ml of 0.1 M Na tetraborate buffer (containing 10% dioxane), pH 8.0. 28 µl of GMBS solution (5 mg of N-succinimidyl γ-maleimidobutyrate/ml of dioxane) are added. After the mixture has reacted at RT for 1 hour, it is rebuffered in 0.1 M phosphate buffer (contains 5 mM EDTA), pH 6.0, by means of a PD10/G25m column. The resulting eluate ("solution 1") has a volume of 2 ml and a concentration of 0.9 mg of streptavidin/ml.

b) 7 mg of triiodothyronine (T3) are dissolved in 700 µl of DMSO. 10 µl of N-ethylmorpholine and 1.6 mg of SAMSA (S-acetylmercaptosuccinic anhydride), dissolved in 80 µl of DMSO, are added. After 30 minutes, 100 µl of a 1 M aqueous solution of hyroxylamine are pipetted in. The resulting solution ("solution 2") is incubated at RT for 15 minutes.

c) 1.76 ml of solution 1 and 41.5 µl of solution 2 are mixed and left to stand at RT for 1 hour. Rebuffering in 0.1 M K phosphate buffer, pH 7.2, ("solution 3") subsequently takes place by means of a PD25/G25m column. After the rebuffering, the concentration of streptavidin-T3 conjugate is 0.6 mg/ml.

Step 2: Labeling of the streptavidin-T3 conjugate with BeriLux label a) Synthesis of the BeriLux label having a biotin group: 200 mg (0.26 mmol) of BeriLux label (possessing an NHS-reactive group) are initially introduced into 30 ml of acetonitrile, and a solution of 98 mg (0.26 mmol) of N-biotin-1,8-diamino-3,6-dioxaoctane (Boehringer Mannheim) and 46 µl (0.3 mmol) of triethylamine in 5 ml of acetonitrile is added dropwise at RT; the reaction mixture is then stirred at RT for 12 h, during which time it becomes green in color. The mixture is filtered and the solvent is distilled off in vacuo. The residue (400 mg; green oil) is purified by preparative medium pressure chromatography (Buchi system) on a reversed-phase column [stationary phase: LichroPrep C-18 (from Merck); mobile phase: gradient of acetonitrile/water=33:67+0.16 by vol of trifluoroacetic acid after acetonitrile/water=45:55+0.1% by vol of trifluoroacetic acid]. 170 mg of a yellow powder are isolated after distilling off the acetonitrile in vacuo and removing the water by freeze drying. MS (FAB): $[C_{47}H_{55}N_6O_9S_2]^+$ (calculated: 911.347; found: 911.350) $[OF_3co_2]^-$ (113).

b) 182 µl of solution 3 (0.1 mg of streptavidin-T3 conjugate), 718 µl of 0.1 M K phosphate buffer, pH 7.2, 14 µl of acetonitrile and 86 µl of a labeling solution [10 mg of BeriLux label (possessing a biotin group)/ml of acetonitrile] are pipetted together and incubated at RT for 30 minutes. The tracer is purified by gel chromatography through PD25/G25m.

Preparation of the Tracer Solution 6 ng of tracer/ml of tracer buffer tracer buffer: 100 mM PBS, pH 6.3, containing 0.29 bovine IgG, 0.1 Mergal and 0.025% ANS.

T3 Standards:

T3 standards were employed in a serum medium in a concentration range of from 0 to 7.5 ng/ml.

Measuring Buffer:

100 mM Tris buffer, pH 8.0, containing 150 mM NaCl, 1% Tween 20 and 0.01% sodium azide.

Assay Implementation:

50 µl of sample were incubated at 37° C. for 30 minutes together with 100 µl of tracer and 20 µl of solid phase A. 10 µl of solid phase B were subsequently added, and 200 µl of measuring buffer were pipetted in after the mixture had been incubated at RT for 10 minutes. The suspension was measured for 1 s in a luminometer (DeriLux® analyzer) (emitting reagents: R1=20 mM nitric acid containing 0.5% hydrogen peroxide; R2=125 mM sodium hydroxide).

Figure 13A:
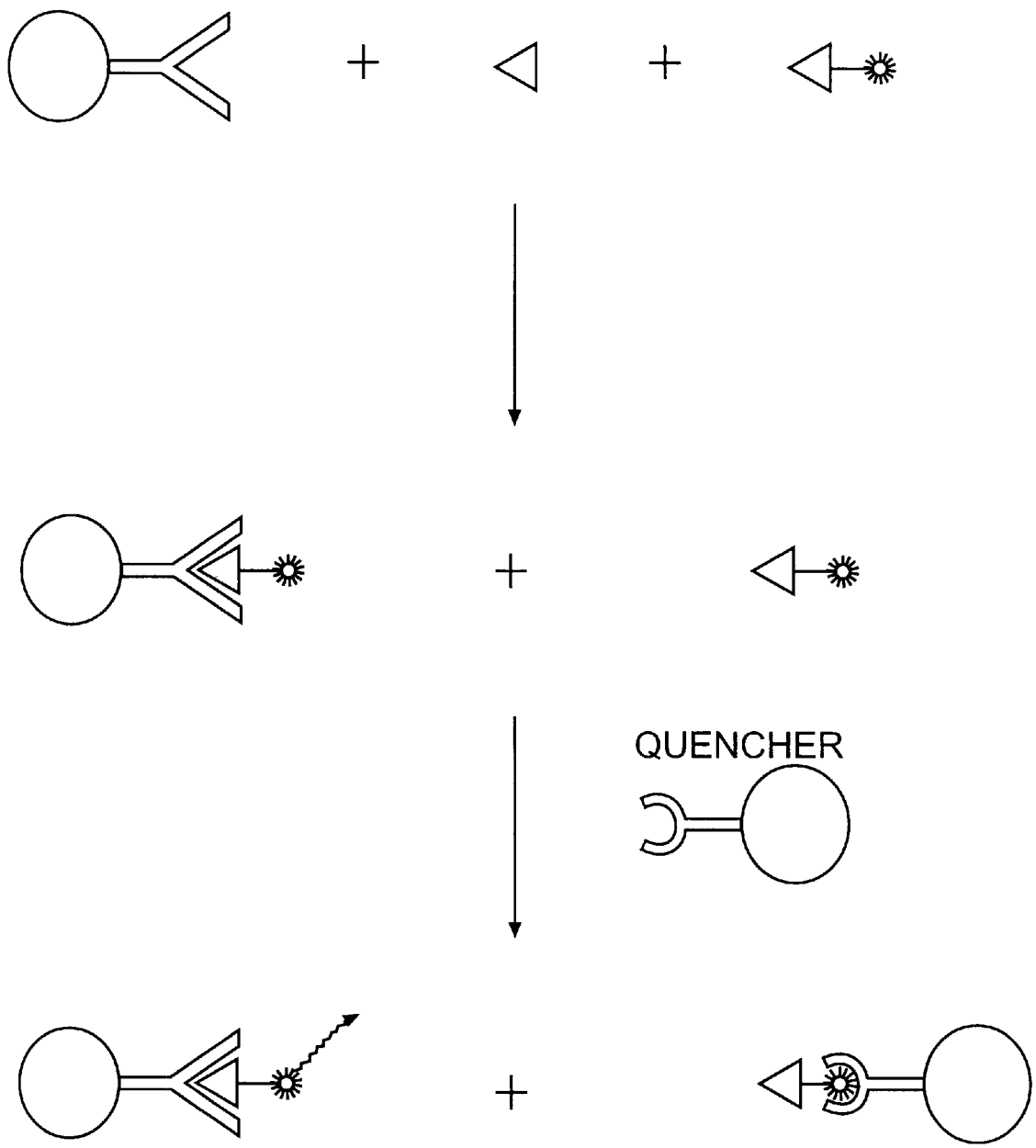
Figure 16:
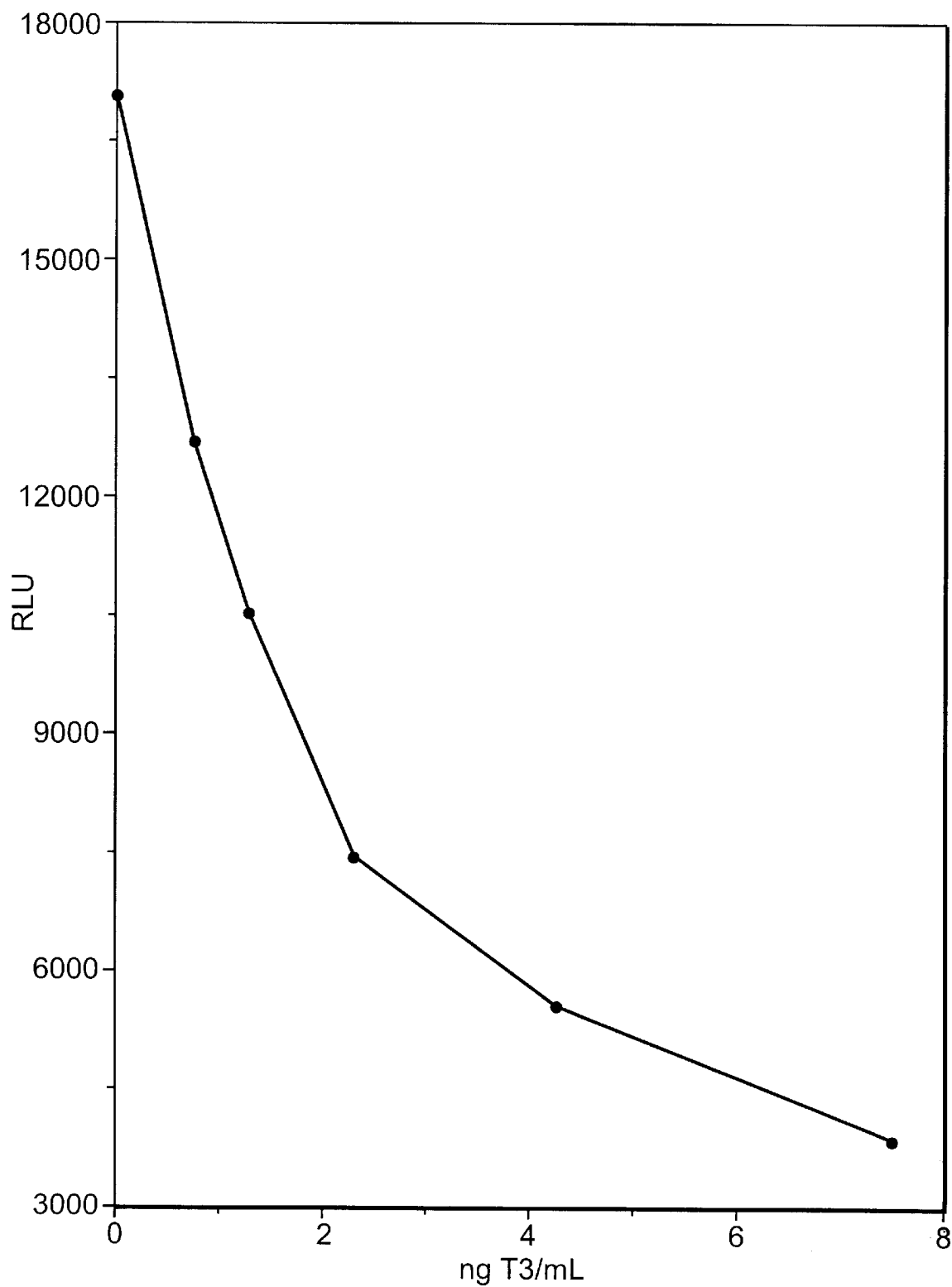
FIG. 16 shows a standard curve of LIA for determining T3.

The results are depicted in FIG. 16 and the assay implementation is depicted schematically in FIG. 13a.

Legend to FIG. 3

The figure shows the quenching effect of three different anti-label antibodies on a tracer antibody which is labeled with a BeriLux® label (acridinium acylsulfonamide label) (signal activity without adding an anti-label antibody= 100%). Whereas the antibody BW 90-9/016 is particularly suitable for protecting the label from signal-altering reagents, BW 90-8/04 can be employed as a signal-altering (in this case, signal-quenching) antibody. BW 89-191/019 is less well suited for either of these applications.

The measuring time in the BeriLux® analyzer is 1 second.

We claim:

1. A method for immunometrically detecting and/or determining the concentration of an analyte, comprising the steps of:
   1) contacting a sample containing the analyte with:
      a) a labeled tracer, which binds to the analyte to form a labeled complex;
      b) a receptor A, which binds to the labeled complex;
      c) a receptor B, which binds to the labeled tracer and generates or alters, a signal by interacting with the labeled tracer,
         wherein receptors A and B are immobilized at a distance sufficient to prevent all or most of the labeled complexes from simultaneously binding to both an A and a B receptor;
   2) determining a signal generated by the labeled tracer;
   3) analyzing the signal to detect and/or determine the concentration of analyte in the sample.

2. The method of claim 1, wherein
   1) receptor A is immunologically reactive with the analyte, and
   2) the labeled tracer is immunologically reactive with the analytes.

3. The method of claim 1, wherein the receptor A and the labeled tracer are directed against different immunological epitopes.

4. The method of claim 1, wherein
   1) the analyte possesses multiple identical epitopes and
   2) receptor A and the labeled tracer are directed against the multiple identical epitopes.

5. The method of claim 1, wherein receptors A and B are immobilized by binding to, or embedding in, different phases.

6. The method of claim 5, wherein at least one phase comprises a plastic surface.

7. The method of claim 5, wherein at least one phase is an inner or outer surface of a solid body.

8. The method of claim 6, wherein the solid body is a membrane, a small tube, or a microtitration plate.

9. The method of claim 5, wherein at least one phase comprises one or more metal-containing and/or metal ion-containing plastic beads.

10. The method of claim 5, wherein at least one phase comprises one or more magnetizable plastic beads.

11. The method of claim 5, wherein the phases are different gel layers.

12. The method of claim 1, wherein the receptors A and B are immobilized by binding to the same phase.

13. The method of claim 12, wherein receptors A and B are immobilized on a fiber.

14. The method of claim 1, wherein the labeled tracer contains a group which is capable of luminescence, fluorescence, phosphorescence, chemiluminescence, bioluminescence, or electroluminescence.

15. The method of claim 1, wherein the labeled tracer contains an acridinium ester, an acridinium acylsulfonamide, a luminol, an isoluminol, a dioxetane, a luciferein, an oxalate, or an oxalic amide.

16. The method of claim 1, wherein the labeled tracer contains an enzyme or a modified enzyme.

17. The method of claim 1, wherein the labeled tracer contains an enzyme substrate.

18. The method of claim 1, wherein the labeled tracer comprises a label directly bound to a receptor.

19. The method of claim 1, wherein the labeled tracer comprises a label indirectly bound to a receptor.

20. The method of claim 1, wherein the receptor B is a monoclonal antibody, a polyclonal antibody, an antibody fragment, a chemically modified antibody, or a chemically modified antibody fragment.

21. The method of claim 1, wherein receptor B is an enzyme inhibitor, avidin, or streptavidin.

22. The method of claim 1, wherein
   1) the labeled receptor contains an acridinium compound and
   2) the receptor B possesses a double helical DNA structure.

23. The method of claim 22, wherein binding of the acridinium compound to the receptor B quenches or alters the emission of light from the acridinium compound.

24. The method of claim 1, further comprising contacting the sample with a receptor B', which binds to the labeled tracer and alters a signal generated by the labeled tracer.

25. The method of claim 24, wherein the binding of the labeled tracer by receptor B does not bring about a direct change in the signal.

26. The method of claim 1, wherein, after the sample, labeled tracer, receptor A and receptor B have been incubated, a liquid is added in order to decrease the sample proportion during the determination of the signal provoked by the labeled tracer.

27. The method of claim 1, wherein, after the sample, labeled tracer, receptor A have been incubated, receptor B is added in a liquid volume which is greater than that of the sample which is used.

28. A method for immunometrically detecting and/or determining the concentration of an analyte, comprising the steps of:
   1) contacting a sample containing the analyte with:
      a) a labeled tracer, which binds to the analyte to form a labeled complex;
      b) a receptor A, which binds to the labeled complex;
      c) a receptor B, which binds to the labeled tracer and generates or alters a signal by interacting with the labeled tracer,
         wherein receptor A and the labeled tracer are immobilized at a distance sufficient to prevent all or most of the labeled complexes from simultaneously binding to both a receptor A and to a labeled tracer;
   2) determining a signal generated by the labeled tracer; and
   3) analyzing the signal to detect and/or determine the concentration of analyte in the sample.

* * * * *

UNITED STATES PATENT AND TRADEMARK OFFICE
CERTIFICATE OF CORRECTION

PATENT NO. : 6,013,457
DATED : January 11, 2000
INVENTOR(S) : Stephan Neuenhofer et al.

It is certified that error appears in the above-identified patent and that said Letters Patent is hereby corrected as shown below:

On the Title Page, Item [57], in the Abstract, line 4, "from" should read --form--.

Claim 1, Column 21, Line 21, after "alters", delete ",".

Claim 2, Column 21, Line 35, "analytes" should read --analyte--.

Claim 27, Column 22, Line 41, before "receptor A", insert --and--.

Signed and Sealed this

Third Day of April, 2001

*Attest:*

NICHOLAS P. GODICI

*Attesting Officer*     *Acting Director of the United States Patent and Trademark Office*